(12) United States Patent
Ohata et al.

(10) Patent No.: US 12,144,536 B2
(45) Date of Patent: Nov. 19, 2024

(54) ENDOSCOPIC TREATMENT INSTRUMENT

(71) Applicant: KANEKA CORPORATION, Osaka (JP)

(72) Inventors: Ken Ohata, Tokyo (JP); Hirokazu Kamakura, Okaya (JP)

(73) Assignee: KANEKA CORPORATION, Osaka (JP)

(*) Notice: Subject to any disclaimer, the term of this patent is extended or adjusted under 35 U.S.C. 154(b) by 580 days.

(21) Appl. No.: 17/440,399

(22) PCT Filed: Feb. 6, 2020

(86) PCT No.: PCT/JP2020/004502
§ 371 (c)(1),
(2) Date: Sep. 17, 2021

(87) PCT Pub. No.: WO2020/195210
PCT Pub. Date: Oct. 1, 2020

(65) Prior Publication Data
US 2022/0151680 A1    May 19, 2022

(30) Foreign Application Priority Data
Mar. 22, 2019  (JP) .................. 2019-055565

(51) Int. Cl.
*A61B 18/14* (2006.01)
*A61B 18/00* (2006.01)

(52) U.S. Cl.
CPC .... *A61B 18/14* (2013.01); *A61B 2018/00601* (2013.01); *A61B 2018/1475* (2013.01)

(58) Field of Classification Search
CPC . A61B 18/14; A61B 18/1477; A61B 18/1492; A61B 2018/00196;
(Continued)

(56) References Cited

U.S. PATENT DOCUMENTS 7,731,714 B2* 6/2010 Miyajima .......... A61B 18/1492
606/49
8,048,073 B2* 11/2011 Nakamura ........ A61B 18/1492
606/41
(Continued)

FOREIGN PATENT DOCUMENTS

| JP | 2008-295609 A | 12/2008 |
| JP | 2010-42200 A  | 2/2010  |
| JP | 2013-85859 A  | 5/2013  |

OTHER PUBLICATIONS

International Search Report, issued in PCT/JP2020/004502, PCT/ISA/210, dated Apr. 21, 2020.
(Continued)

*Primary Examiner* — Michael F Peffley
(74) *Attorney, Agent, or Firm* — Birch, Stewart, Kolasch & Birch, LLP

(57) ABSTRACT

Provided is an endoscopic treatment instrument that can maintain a state where the treatment instrument protrudes, by a simple manipulation and that can keep an amount of protrusion of the treatment instrument constant. The endoscopic treatment instrument (1) has an operation unit having: an operation unit body (50) fixed to a cylindrical member; and a slider (60) that is fixed to a linear object and is slidable with respect to the operation unit body (50) in the longitudinal direction. The operation unit is provided with a first stop position and a first stop release position distal to the first stop position, the first stop position being a position where the operation unit body (50) and the slider (60) contact each other as a result of relative movement of the operation unit body (50) and the slider (60).

13 Claims, 12 Drawing Sheets

(58) Field of Classification Search
CPC ........... A61B 2018/00601; A61B 2018/00946;
A61B 2018/1412; A61B 2018/1475
USPC .................................................. 606/45–47
See application file for complete search history.

(56) References Cited

U.S. PATENT DOCUMENTS

| | | | | |
|---|---|---|---|---|
| 8,187,271 B2* | 5/2012 | Yahagi | ............... | A61B 18/1492 |
| | | | | 606/41 |
| 2005/0072280 A1* | 4/2005 | Ono | ................... | A61B 18/1402 |
| | | | | 83/13 |
| 2010/0016867 A1 | 1/2010 | Itoh | | |

OTHER PUBLICATIONS

Written Opinion of the International Searching Authority, issued in PCT/JP2020/004502, PCT/ISA/237, dated Apr. 21, 2020.

* cited by examiner

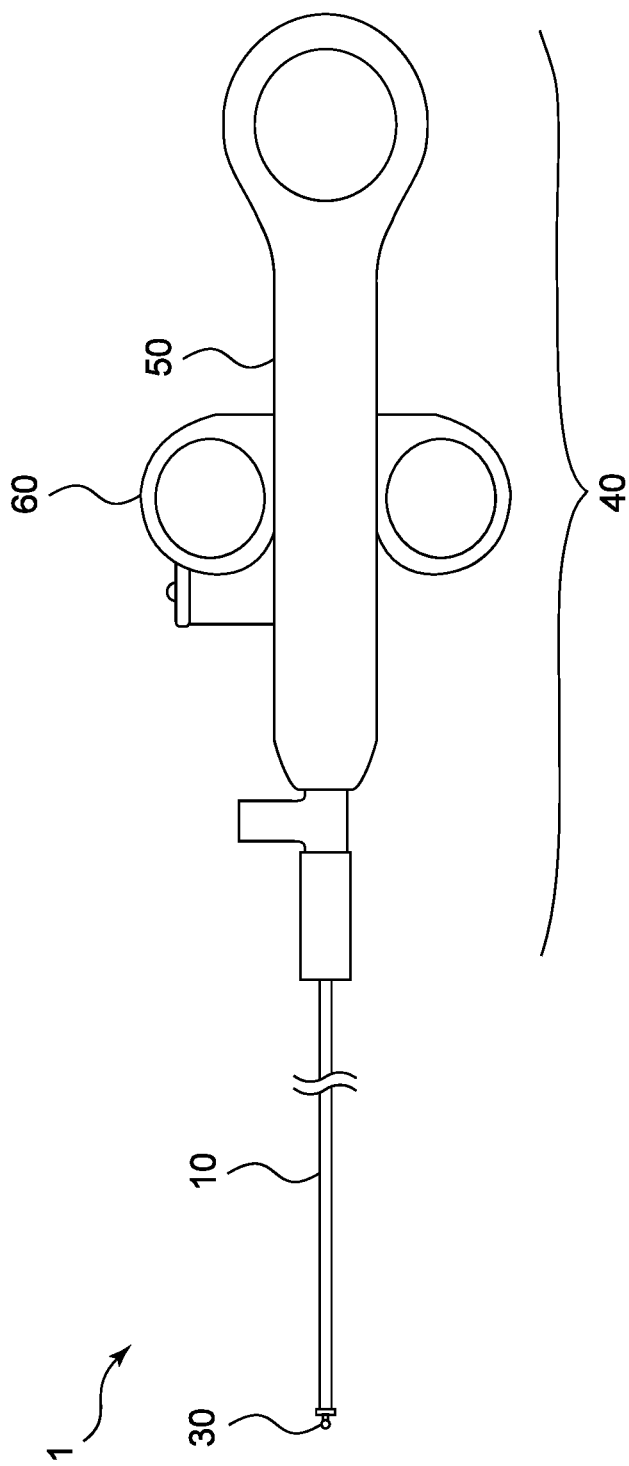
[FIG. 1]

【FIG. 2(a)】
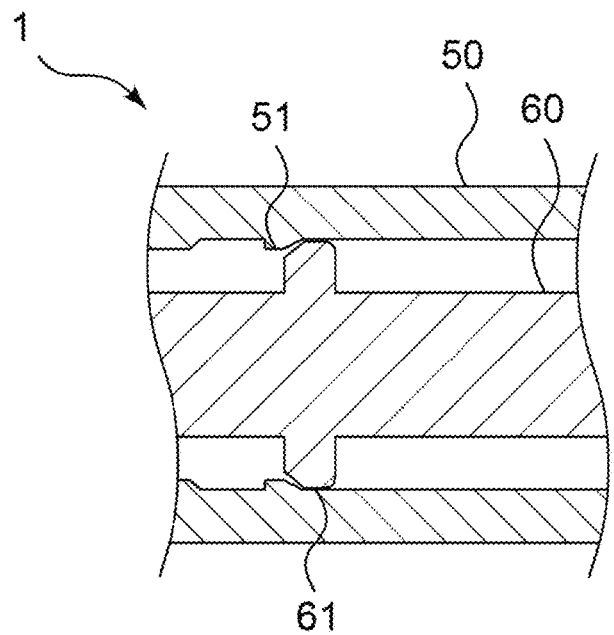
【FIG. 2(b)】
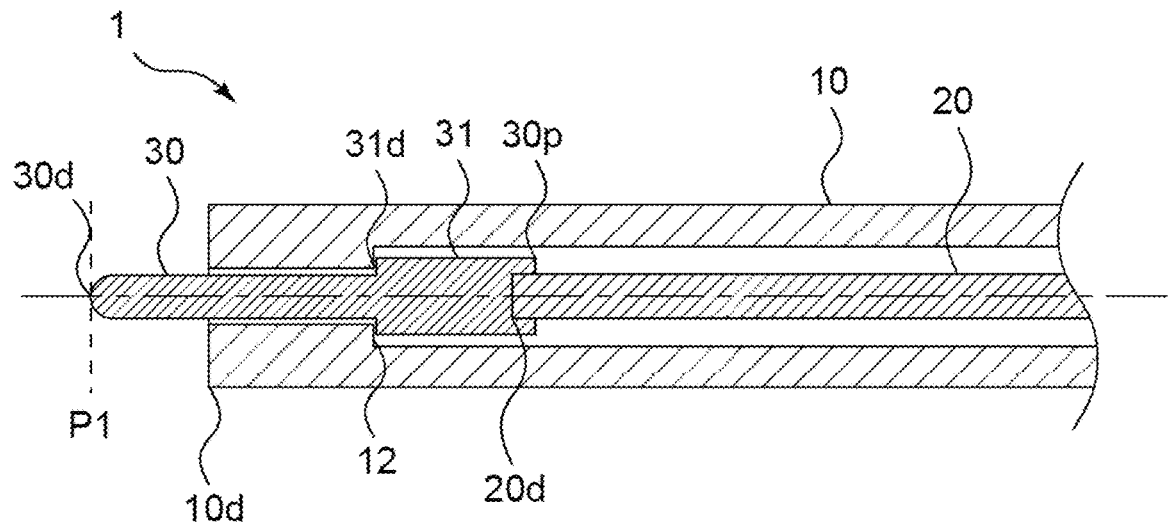

[FIG. 2(c)]
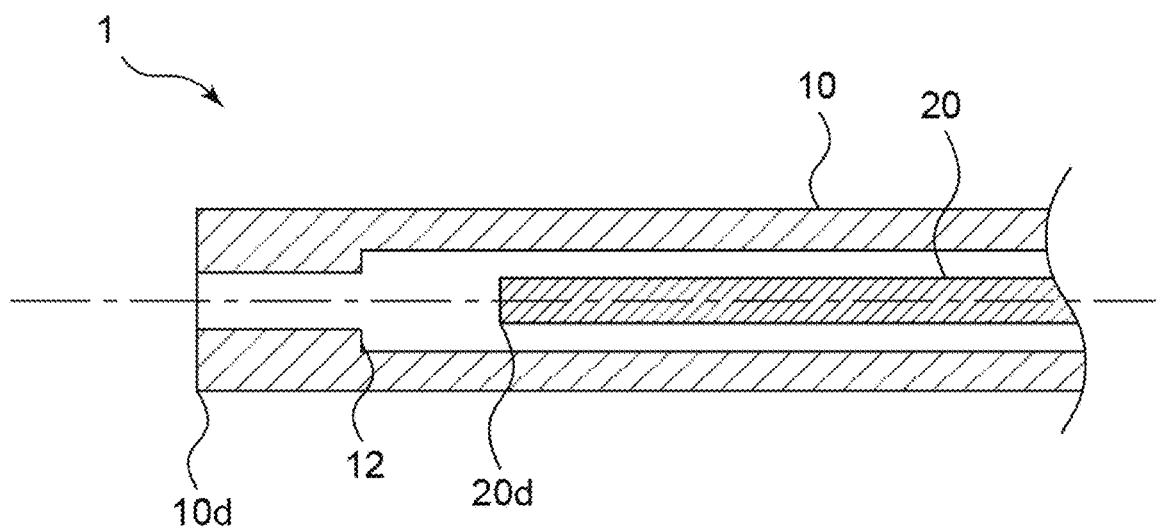

[FIG. 3(a)]
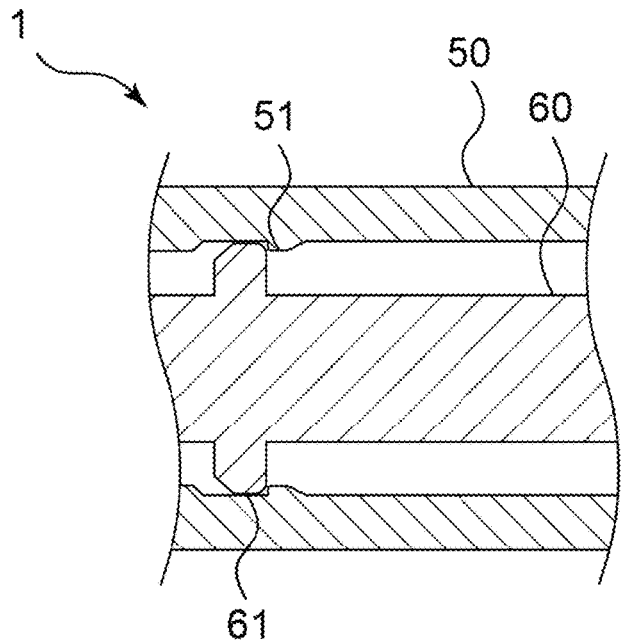
[FIG. 3(b)]
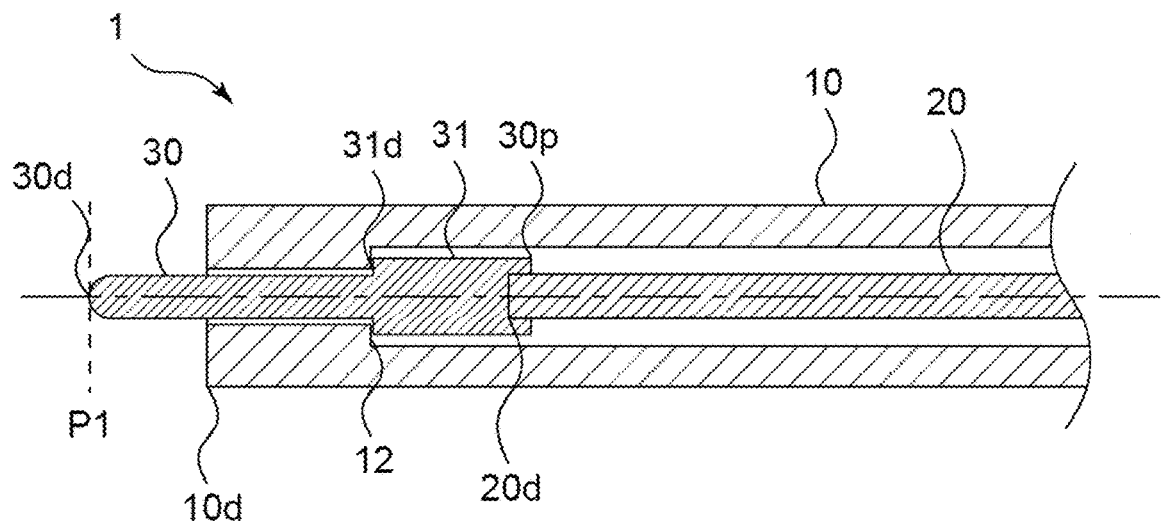

[FIG. 3(c)]
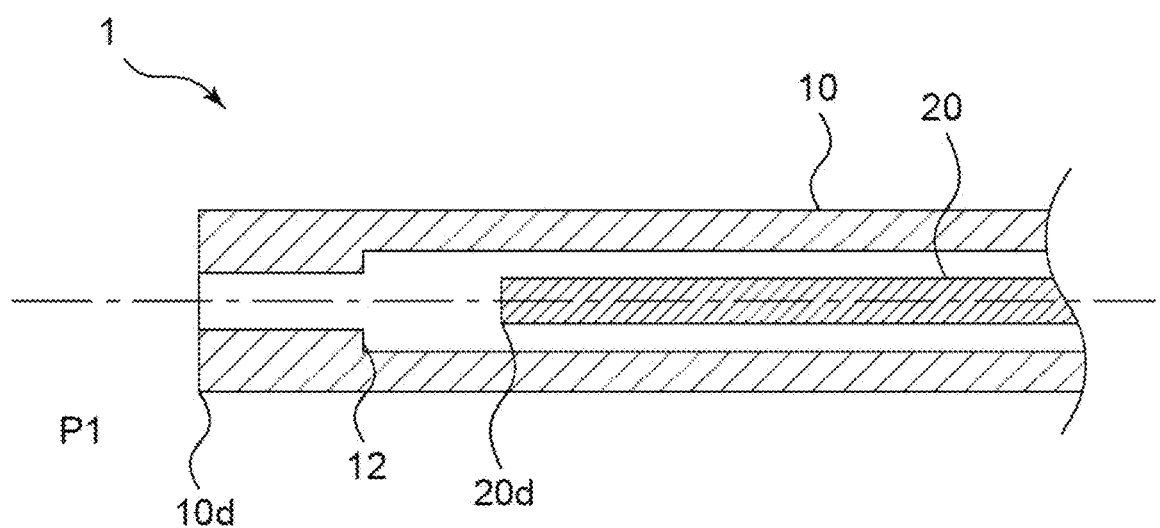

[FIG. 4(a)]
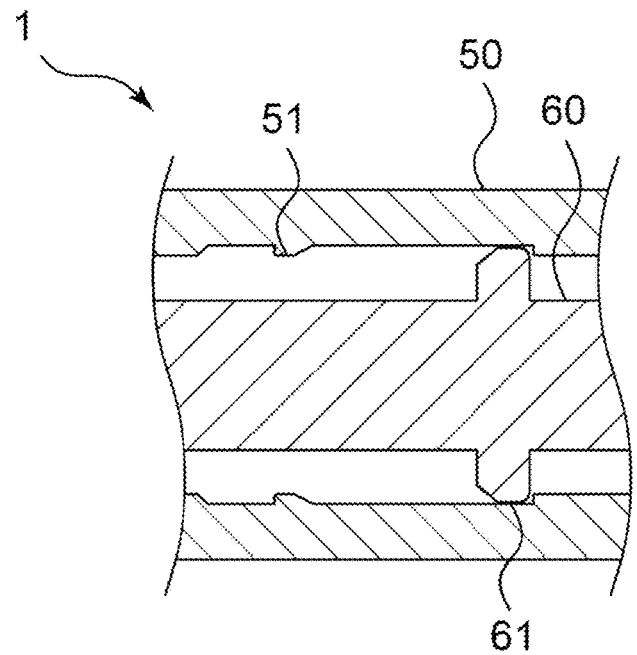
[FIG. 4(b)]
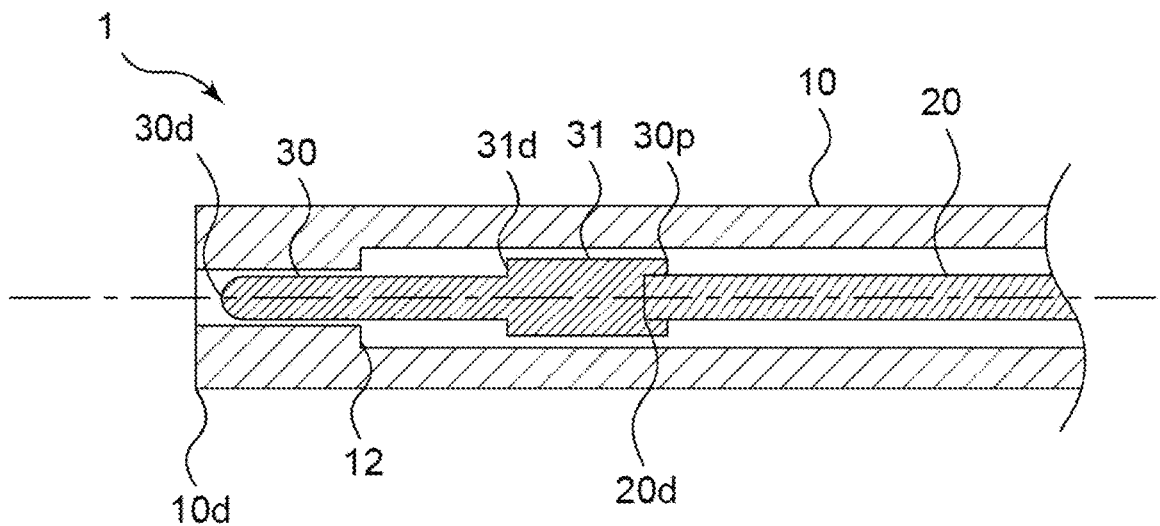

[FIG. 4(c)]
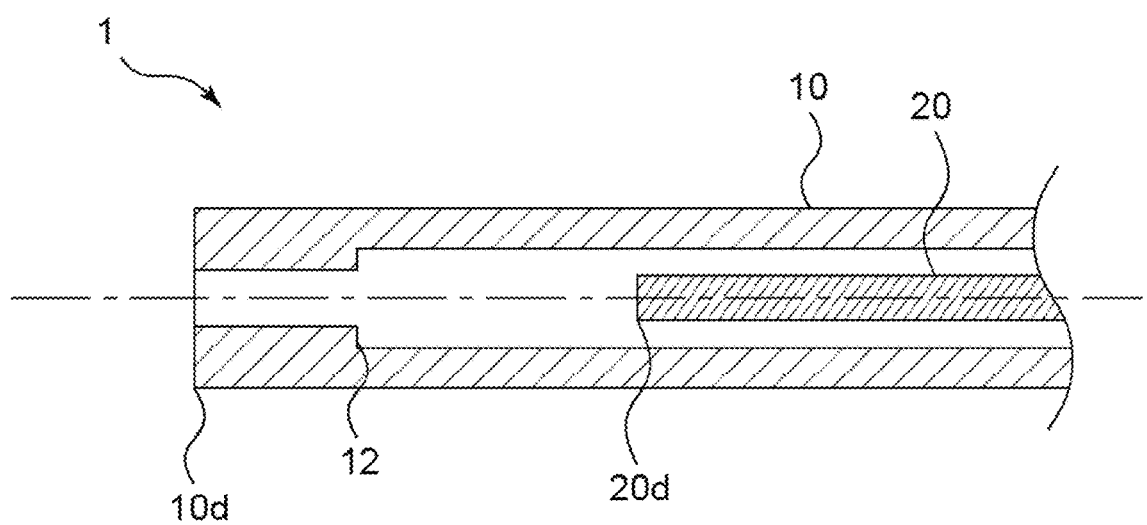

[FIG. 5]
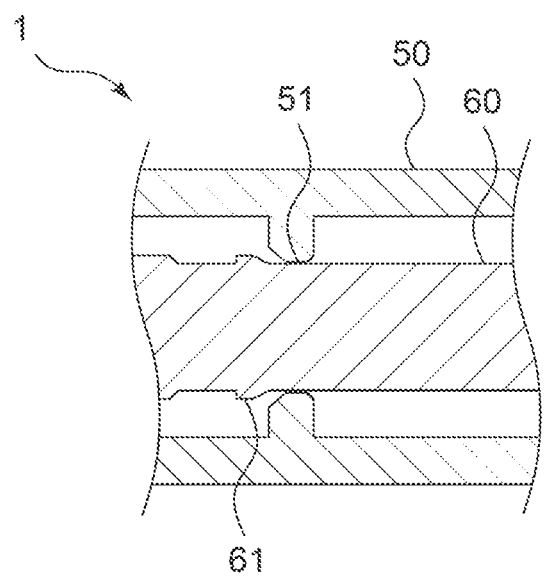

【FIG. 6(a)】
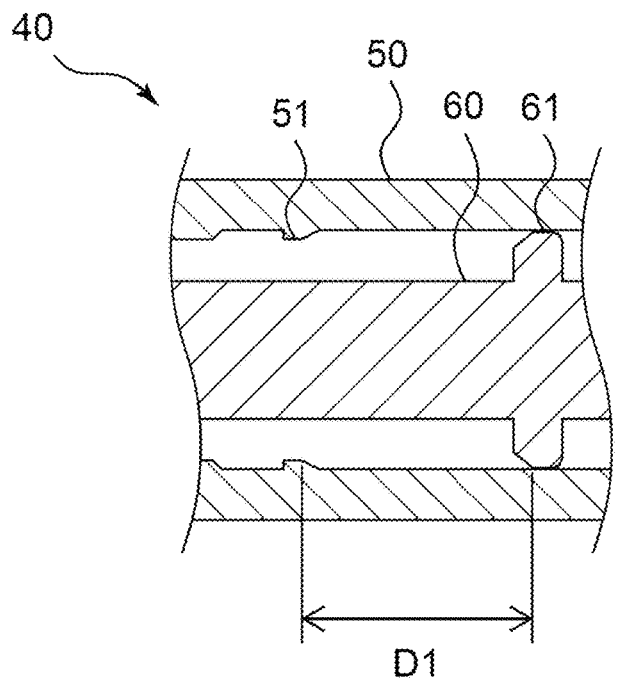
【FIG. 6(b)】
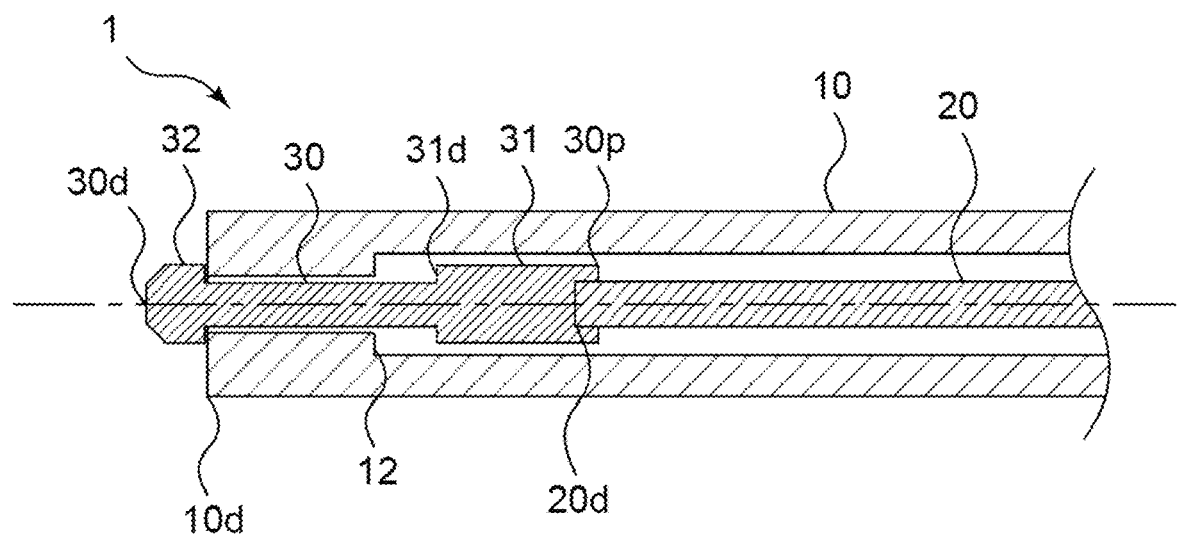

[FIG. 7(a)]
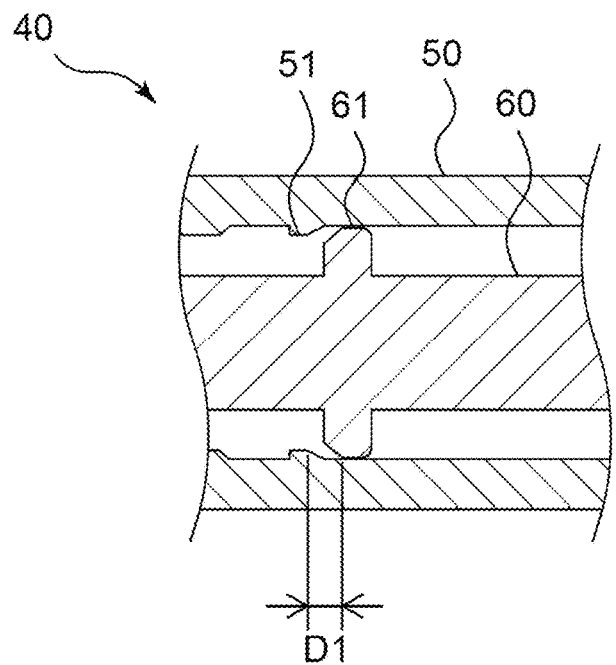
[FIG. 7(b)]
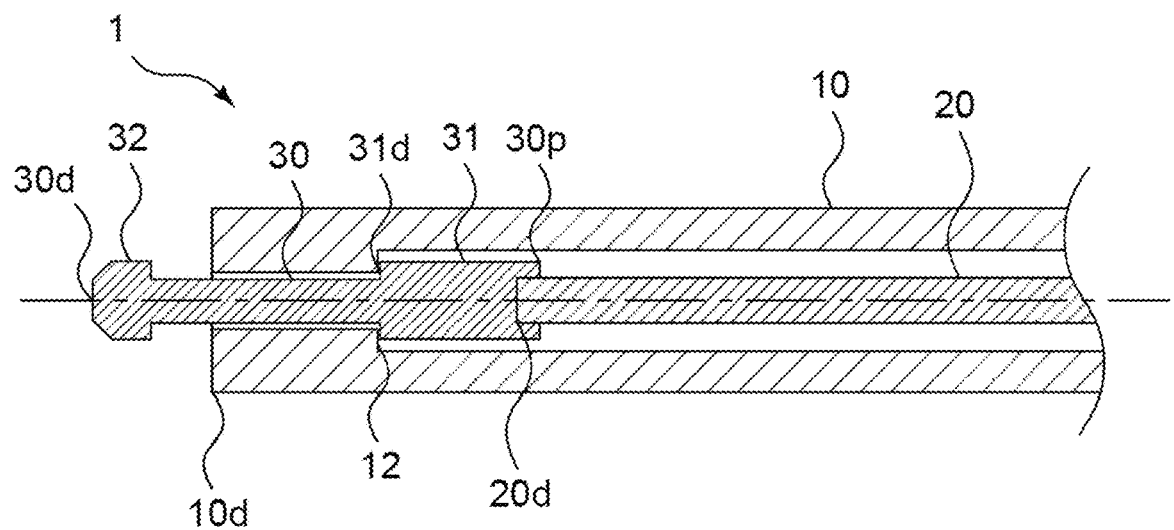

[FIG. 8(a)]
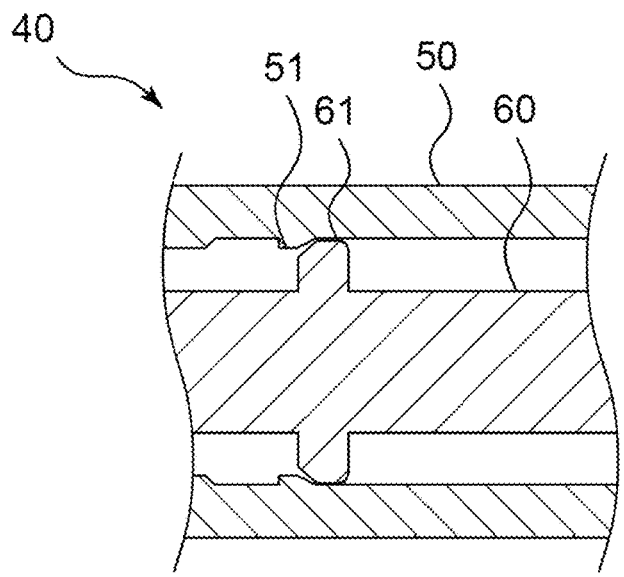
[FIG. 8(b)]
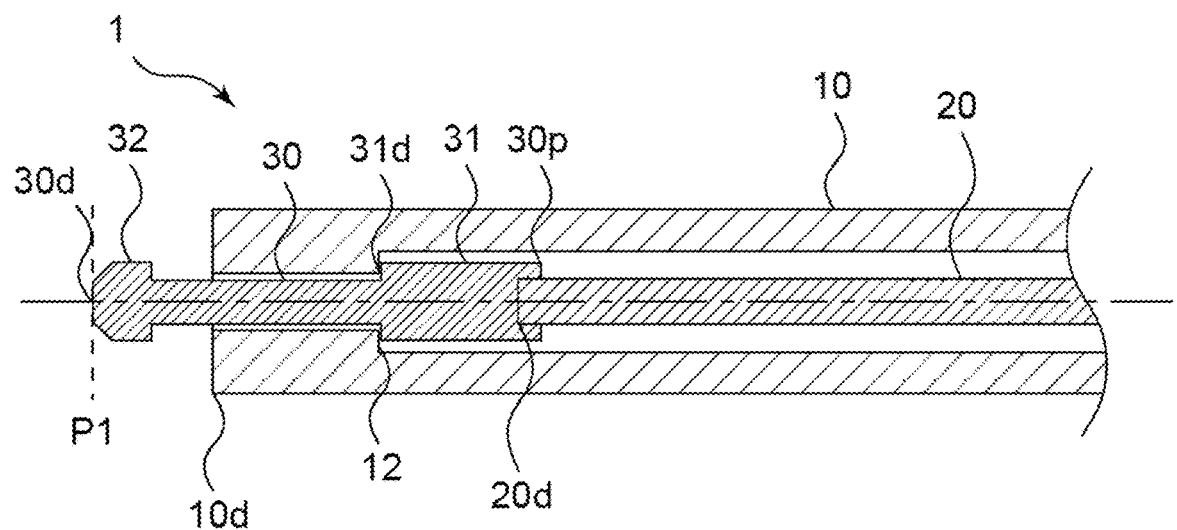

[FIG. 9(a)]
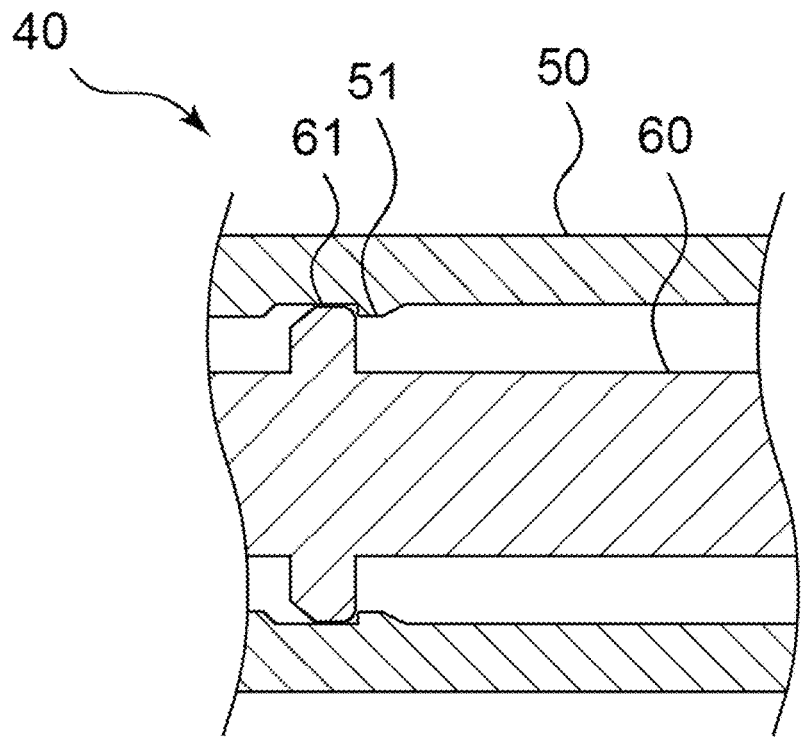
[FIG. 9(b)]
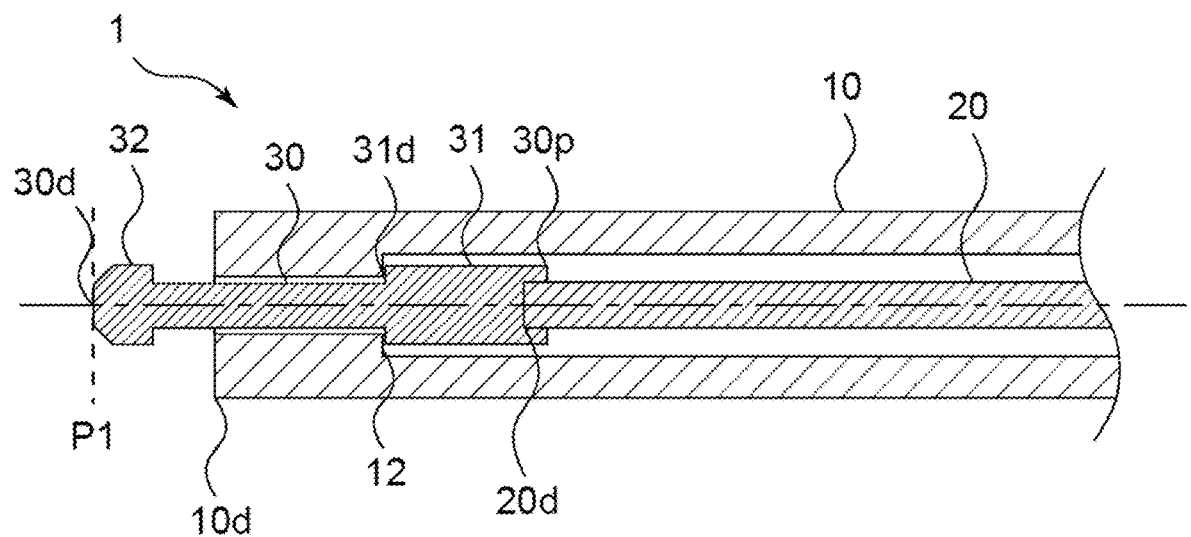

ENDOSCOPIC TREATMENT INSTRUMENT

CROSS REFERENCE TO RELATED APPLICATIONS

The present application is the U.S. National Phase of PCT International Application No. PCT/JP2020/004502, filed on Feb. 6, 2020, which claims priority under 35 U.S.C. 119 (a) to Patent Application No. 2019-055565, filed in Japan on Mar. 22, 2019, all of which are hereby expressly incorporated by reference into the present application.

TECHNICAL FIELD

The present invention relates to a treatment instrument that is introduced into a living body via an endoscope in surgery or treatment using the endoscope. More specifically, the present invention relates to an endoscopic high-frequency treatment instrument including a conductive tip that is supplied with a high-frequency current and that is used for incision of a tissue or the like.

BACKGROUND ART

An endoscopic treatment instrument, which is a treatment instrument such as a knife for excising a lesion site using high frequency, is used for treatment using an endoscope such as endoscopic submucosal dissection (ESD) and endoscopic mucosal resection (EMR). In treatment using an endoscope such as ESD and EMR, a lesion site is gradually peeled off or excised with the amount of protrusion of the endoscopic treatment instrument being kept constant.

In a procedure of gradually peeling off a lesion site such as ESD, the procedure time may reach one hour or more depending on the state of the lesion site. During the procedure, it is necessary to keep the amount of protrusion of the treatment instrument, which is an endoscopic treatment instrument, constant. Conventionally, the operator needs to continuously apply a force to a manipulation portion of the endoscopic treatment instrument in order to keep the amount of protrusion of the treatment instrument, and, due to a manipulation error or fatigue of the operator, the amount of protrusion of the treatment instrument is changed or a state where the treatment instrument protrudes is not obtained during the procedure in some cases.

For example, Patent Document 1 describes an endoscopic forward-protrusion-type treatment instrument which is configured such that a tip treatment member protrudes forward from the tip of a flexible sheath and advances/retreats by manipulating a flexible manipulation wire, which is inserted into the flexible sheath, such that the manipulation wire advances/retreats in the axial direction. The treatment instrument is provided with biasing means for biasing the tip treatment member in a direction in which the tip treatment member protrudes forward from the tip of the flexible sheath, and the manipulation portion is provided with manipulation member locking means for freely locking and unlocking a slide manipulation portion with respect to a manipulation portion body in a state where the tip treatment member is pulled toward the tip side of the flexible sheath against the biasing force of the biasing means. Patent Document 2 describes a clip treatment instrument including: a sheath; a manipulation wire disposed inside the sheath; a handle body which is connected to the sheath and in which the manipulation wire is disposed; a slider which is mounted on the outer periphery of the handle body and configured to move the manipulation wire in the axial direction; and a wire position fixing mechanism which is configured to temporarily fix the manipulation wire in a state where the manipulation wire protrudes from the tip of the sheath by a certain length. By moving the slider in the axial direction, the manipulation wire inside the sheath is moved in the direction in which the sheath extends. Patent Document 3 describes a medical instrument in which a manipulation wire is inserted into a sheath so as to be able to move forward and backward inside the sheath, and a treatment portion is provided at the tip of the manipulation wire. When the manipulation wire is moved forward to the distal side of the sheath, the treatment portion enters an operating state, and when the manipulation wire is moved backward to the proximal side of the sheath, the treatment portion enters a non-operating state. A manipulation body is provided on the proximal side of the sheath, and causes the treatment portion to shift to a non-operating state or an operating state by moving the tip of the manipulation wire forward or backward.

PRIOR ART DOCUMENTS

Patent Documents

Patent Document 1: JP-A-2008-295609
Patent Document 2: JP-A-2010-42200
Patent Document 3: JP-A-2013-85859

SUMMARY OF INVENTION

Problems to be Solved by the Invention

However, in the endoscopic treatment instruments as described in Patent Documents 1 to 3, there is a problem that the treatment instrument may retreat into the tubular member when another object comes into contact with the tip of the treatment instrument, a problem that it takes time and effort to perform a manipulation for keeping the amount of protrusion of the treatment instrument constant, or a problem that the defective rate at the time of manufacture is high and the cost is high since the configuration of the manipulation portion is complicated. Thus, it is considered that there is room for improvement of such endoscopic treatment instruments.

The present invention has been made in view of the above circumstances, and an object of the present invention is to provide an endoscopic treatment instrument that can maintain a state where the treatment instrument protrudes, by a simple manipulation and that can keep an amount of protrusion of the treatment instrument constant.

Solutions to the Problems

A first endoscopic treatment instrument of the present invention that has solved the above problems comprising: a tubular member having a distal end and a proximal end and having an inner cavity extending in a long axis direction thereof, a linear member having a distal end and a proximal end, extending in the long axis direction, and disposed in the inner cavity of the tubular member; a conductive tip provided on a distal side of the linear member; and a manipulation portion provided on a proximal side of the linear member, wherein the manipulation portion has a manipulation portion body to which a proximal end portion of the tubular member is fixed, and a slider to which a proximal end portion of the linear member is fixed and which is slidable relative to the manipulation portion body in the long axis direction, the manipulation portion has a primary stop point where the manipulation portion body and the slider come into contact with each other by relative movement of the manipulation portion body and the slider, and a primary stop release point on the distal side with respect to the primary stop point, the conductive tip can be caused to protrude from the tubular member by moving the slider from the proximal side to the distal side, and the following [Condition 1] and [Condition 2] are satisfied,

[Condition 1]

in a state where the conductive tip is not provided to the linear member, (1) by moving the slider relative to the manipulation portion body toward the distal side, at least a part of the slider comes into contact with at least a part of the manipulation portion body at the primary stop point located in a movable range of the slider, whereby movement of the slider in a distal direction is stopped, (2) the slider is moved from the primary stop point in the distal direction by applying a pushing force equal to or larger than a predetermined force to the slider, and (3) at the primary stop release point located in the movable range of the slider, the slider can be moved in the distal direction even when a pushing force applied to the slider is less than the predetermined force, and

[Condition 2]

in a state where the conductive tip is provided to the linear member, when the slider is at the primary stop point, or when the slider is at the primary stop release point, a distal end portion of the conductive tip is located at a first position located on the distal side with respect to the distal end of the tubular member.

The first endoscopic treatment instrument is preferable wherein the manipulation portion further has a secondary stop point where the manipulation portion body and the slider come into contact with each other by relative movement of the manipulation portion body and the slider, the secondary stop point is located on the proximal side in the movable range of the slider with respect to the primary stop point, and in a state where the conductive tip is not provided to the slider, by pulling the slider toward the proximal side, at least a part of the slider comes into contact with at least a part of the manipulation portion body at the secondary stop point to stop movement of the slider in the proximal direction.

The first endoscopic treatment instrument is preferable wherein when the slider is located at the secondary stop point in a state where the conductive tip is provided to the linear member, a distal end of the conductive tip is located on the proximal side with respect to the distal end of the tubular member.

The first endoscopic treatment instrument is preferable wherein when the slider is on the proximal side with respect to the primary stop point in a state where the conductive tip is provided to the linear member, the distal end of the conductive tip is located on the proximal side with respect to the first position.

The first endoscopic treatment instrument is preferable wherein the manipulation portion body has a manipulation portion body side projection on a surface facing the slider, the slider has a slider side projection on a surface facing the manipulation portion body, and contact between at least the part of the slider and at least the part of the manipulation portion body is contact between the manipulation portion body side projection and the slider side projection.

A second endoscopic treatment instrument of the present invention that has solved the above problems comprising: a tubular member having a distal end and a proximal end and having an inner cavity extending in a long axis direction; a linear member having a distal end and a proximal end, extending in the long axis direction, and disposed in the inner cavity of the tubular member; a conductive tip provided on a distal side of the linear member; and a manipulation portion provided on a proximal side of the linear member, wherein the manipulation portion has a manipulation portion body to which a proximal end portion of the tubular member is fixed, and a slider to which a proximal end portion of the linear member is fixed and which is slidable relative to the manipulation portion body in the long axis direction, the conductive tip can be caused to protrude from the tubular member by moving the slider from the proximal side to the distal side, the conductive tip has an enlarged portion having a maximum outer diameter larger than a minimum inner diameter of the tubular member, on the proximal side of the conductive tip, the tubular member has a contact portion which comes into contact with a distal end of the enlarged portion, the manipulation portion body has a manipulation portion body side projection, the slider has a slider side projection, when the slider side projection is located on the proximal side with respect to the manipulation portion body side projection and the manipulation portion body side projection and the slider side projection are spaced apart from each other by a distance equal to or larger than a predetermined distance, the enlarged portion and the contact portion are not in contact with each other, when the slider side projection is located on the proximal side with respect to the manipulation portion body side projection and the manipulation portion body side projection and the slider side projection are spaced apart from each other by a distance less than the predetermined distance, the enlarged portion and the contact portion are in contact with each other, and when the slider side projection is located on the proximal side with respect to the manipulation portion body side projection and the manipulation portion body side projection and the slider side projection are in contact with each other, the enlarged portion and the contact portion are in contact with each other.

The second endoscopic treatment instrument is preferable wherein when the slider side projection is located on the distal side with respect to the manipulation portion body side projection, the enlarged portion and the contact portion are in contact with each other.

The second endoscopic treatment instrument is preferable wherein in a state where a distal side surface of the manipulation portion body side projection and a proximal side surface of the slider side projection are in contact with each other, a distal end portion of the conductive tip is located at a first position located on the distal side with respect to the distal end of the tubular member, and in a state where a proximal side surface of the manipulation portion body side projection and a distal side surface of the slider side projection are in contact with each other, the distal end portion of the conductive tip is located at the first position.

The second endoscopic treatment instrument is preferable wherein when the slider is moved to a most proximal position in a movable range thereof, a distal end of the conductive tip is located on the proximal side with respect to the distal end of the tubular member.

The second endoscopic treatment instrument is preferable wherein a force required for moving the slider side projection from the distal side of the manipulation portion body side projection to the proximal side is larger than a force required for moving the slider side projection from the proximal side of the manipulation portion body side projection to the distal side.

The second endoscopic treatment instrument is preferable wherein the slider side projection has a tapered portion on a distal side surface thereof and has no tapered portion on a proximal side surface thereof, and the manipulation portion body side projection has a tapered portion on a proximal side surface thereof and has no tapered portion on a distal side surface thereof.

The second endoscopic treatment instrument is preferable wherein at least either one of the linear member and the conductive tip has a length absorption portion which shortens a length in the long axis direction of at least either one of the linear member and the conductive tip when a force is applied from the proximal side toward the distal side.

The second endoscopic treatment instrument is preferable wherein the manipulation portion body has no projection on the proximal side with respect to the manipulation portion body side projection.

Effects of the Invention

In the first endoscopic treatment instrument of the present invention, since [Condition 1] and [Condition 2] are satisfied, the amount of protrusion of the conductive tip from the tubular member can be easily made constant, and a state where the treatment instrument protrudes can be maintained. In addition, in the second endoscopic treatment instrument of the present invention, since: the enlarged portion and the contact portion are not in contact with each other when the slider side projection is located on the proximal side with respect to the manipulation portion body side projection and the manipulation portion body side projection and the slider side projection are spaced apart from each other by a distance equal to or larger than the predetermined distance; the enlarged portion and the contact portion are in contact with each other when the slider side projection is located on the proximal side with respect to the manipulation portion body side projection and the manipulation portion body side projection and the slider side projection are spaced apart from each other by a distance less than the predetermined distance; and the enlarged portion and the contact portion are in contact with each other when the slider side projection is located on the proximal side with respect to the manipulation portion body side projection and the manipulation portion body side projection and the slider side projection are in contact with each other, the amount of protrusion of the conductive tip from the tubular member can be kept constant by a simple manipulation, and a state where the treatment instrument protrudes can be maintained.

BRIEF DESCRIPTION OF THE DRAWINGS

FIG. 1 shows an overall view of an endoscopic treatment instrument according to an embodiment of the present invention.

FIG. 2 (a) shows a cross-sectional view including a long axis of a manipulation portion in a state where a slider is at a primary stop point, and FIG. 2 (b) shows a cross-sectional view including a long axis of a distal end portion of the endoscopic treatment instrument in a state where the slider is at the primary stop point. FIG. 2 (c) shows a cross-sectional view including a long axis of a distal end portion of the endoscopic treatment instrument (without a conductive tip) in a state where the slider is at the primary stop point.

FIG. 3 (a) shows a cross-sectional view including the long axis of the manipulation portion in a state where the slider is at a primary stop release point, and FIG. 3 (b) shows a cross-sectional view including the long axis of the distal end portion of the endoscopic treatment instrument in a state where the slider is at the primary stop release point. FIG. 3 (c) shows a cross-sectional view including the long axis of the distal end portion of the endoscopic treatment instrument (without a conductive tip) in a state where the slider is at the primary stop release point.

FIG. 4 (a) shows a cross-sectional view including the long axis of the manipulation portion in a state where the slider is at a secondary stop point, and FIG. 4 (b) shows a cross-sectional view including the long axis of the distal end portion of the endoscopic treatment instrument in a state where the slider is at the secondary stop point. FIG. 4 (c) shows a cross-sectional view including the long axis of the distal end portion of the endoscopic treatment instrument (without a conductive tip) in a state where the slider is at the secondary stop point.

FIG. 5 shows a cross-sectional view including a long axis of a manipulation portion in a state where a slider is at a primary stop point in another embodiment of the present invention.

FIG. 6 (a) shows a cross-sectional view including the long axis of the manipulation portion in a state where a manipulation portion body side projection and a slider side projection are spaced apart from each other by a distance equal to or larger than a predetermined distance, and FIG. 6 (b) shows a cross-sectional view including the long axis of the distal end portion of the endoscopic treatment instrument in a state where the manipulation portion body side projection and the slider side projection are spaced apart from each other by the distance equal to or larger than the predetermined distance.

FIG. 7 (a) shows a cross-sectional view including the long axis of the manipulation portion in a state where the manipulation portion body side projection and the slider side projection are spaced apart from each other by a distance less than the predetermined distance, and FIG. 7 (b) shows a cross-sectional view including the long axis of the distal end portion of the endoscopic treatment instrument in a state where the manipulation portion body side projection and the slider side projection are spaced apart from each other by the distance less than the predetermined distance.

FIG. 8 (a) shows a cross-sectional view including the long axis of the manipulation portion in a state where the manipulation portion body side projection and the slider side projection are in contact with each other, and FIG. 8 (b) shows a cross-sectional view including the long axis of the distal end portion of the endoscopic treatment instrument in a state where the manipulation portion body side projection and the slider side projection are in contact with each other.

FIG. 9 (a) shows a cross-sectional view including the long axis of the manipulation portion in a state where the slider side projection is located on a distal side with respect to the manipulation portion body side projection, and FIG. 9 (b) shows a cross-sectional view including the long axis of the distal end portion of the endoscopic treatment instrument in a state where the slider side projection is located on the distal side with respect to the manipulation portion body side projection.

MODE FOR CARRYING OUT THE INVENTION

Hereinafter, the present invention will be more specifically described based on the following embodiments. However, the present invention is not limited to the following embodiments and, as a matter of course, can also be carried out with appropriate modifications being made within the scope of the gist described above and below, and any of these modifications are included in the technical scope of the present invention. In any of the drawings, hatching, reference characters for members, or the like may be omitted for convenience. In this case, see the description and the other drawings. Since priority is given to facilitating the understanding of the characteristics of the present invention, the dimensions of various members in the drawings may be different from actual dimensions.

The endoscopic treatment instrument of the present invention is inserted into a treatment instrument insertion channel of an endoscope and used for treatment such as incision of a lesion site in a body cavity. The endoscopic treatment instrument of the present invention is used as a high-frequency treatment instrument which is supplied with power from a hand side to generate a current to, for example, excise or cauterize the surface of a body cavity.

In the present invention, an axial direction refers to the long axis direction of a tubular member, a proximal side in the axial direction refers to a direction to the hand side of a user (operator), and a distal side in the axial direction refers to a direction to the treatment portion side and a direction opposite to the proximal side. In addition, in the present invention, a radial direction refers to the radial direction of the tubular member, the inner side in the radial direction refers to the direction toward the center side of the tubular member, and the outer side in the radial direction refers to the radiation direction of the tubular member.

First, a first endoscopic treatment instrument according to an embodiment of the present invention will be described. FIG. 1 shows an overall view of an endoscopic treatment instrument 1, and FIG. 2 to FIG. 4 each show a cross-sectional view including the long axis of the endoscopic treatment instrument 1. As shown in FIG. 1 to FIG. 4, the endoscopic treatment instrument 1 includes a tubular member 10 which has a distal end and a proximal end and has an inner cavity extending in the long axis direction thereof; a linear member 20 which has a distal end and a proximal end, extends in the long axis direction, and is disposed in the inner cavity of the tubular member 10; a conductive tip 30 which is provided on the distal side of the linear member 20; and a manipulation portion 40 which is provided on the proximal side of the linear member 20.

The tubular member 10 has a distal end and a proximal end and has an inner cavity extending in the long axis direction thereof. The linear member 20 is disposed in the inner cavity of the tubular member 10. At least a part of the conductive tip 30 is housed in the inner cavity of the tubular member 10.

As the tubular member 10, for example, a tubular body formed from a synthetic resin, a tubular body formed from a coiled metal or synthetic resin, a tubular body that is made so as to be rotatable in the axial direction by connecting a plurality of short tubular joint pieces, or the like is used. Among them, the tubular member 10 is preferably a tubular body formed from a synthetic resin. If the tubular member 10 is a tubular body formed from a synthetic resin, the tubular member 10 has both flexibility and rigidity. Thus, the tubular member 10 can bend along the inner shape of a body cavity. Furthermore, if the tubular member 10 is a tubular body formed from a synthetic resin, a force applied from the hand side of the endoscopic treatment instrument 1 is easily transmitted to the tip side, so that it is easier to cause the endoscopic treatment instrument 1 to reach a region to be treated.

Examples of the synthetic resin forming the tubular member 10 include: polyamide-based resins such as nylon; polyolefin-based resins such as polyethylene and polypropylene; polyester-based resins such as polyethylene terephthalate (PET); aromatic polyether ketone-based resins such as polyether ether ketone (PEEK); polyimide-based resins; and fluorine-based resins such as polytetrafluoroethylene (PTFE), tetrafluoroethylene-perfluoroalkyl vinyl ether copolymer (PFA), and ethylene-tetrafluoroethylene copolymer (ETFE). Among them, the material forming the tubular member 10 is preferably a fluorine-based resin, and more preferably PTFE or PFA. If the tubular member 10 is formed from a fluorine-based resin, the slipperiness of the surface of the tubular member 10 can be improved, so that it is easy to insert the endoscopic treatment instrument 1 into the treatment instrument insertion channel of the endoscope and send the endoscopic treatment instrument 1 to a region to be treated.

The material forming the tubular member 10 is preferably transparent or translucent. If the tubular member 10 is formed from a transparent or translucent material, the user can visually confirm the positional relationship between the tubular member 10 and the conductive tip 30 disposed in the inner cavity of the tubular member 10, so that it is easier to cause the conductive tip 30 to protrude or retract from or into the tubular member 10. The tubular member 10 may be provided with a portion having a color different from the color of the other portion in a portion within the field of view of the endoscope, and the portion having a color different from the color of the other portion may be used as a visual marker.

As the length in the long axis direction of the tubular member 10, an appropriate length can be selected in consideration of the distance from the forceps port of the endoscope to a region to be treated, etc., and the length in the long axis direction of the tubular member 10 can be, for example, not shorter than 1000 mm and not longer than 3000 mm.

The linear member 20 has a distal end and a proximal end, extends in the long axis direction, and is disposed in the inner cavity of the tubular member 10. The conductive tip 30 is connected to the distal side of the linear member 20. The linear member 20 allows the conductive tip 30 to protrude or retract from or into the distal end 10d of the tubular member 10 by advancing or retreating the linear member 20 in the long axis direction.

The linear member 20 is preferably solid, but may have a tubular shape with an inner cavity extending in the long axis direction. If the linear member 20 is solid, even when the linear member 20 has a smaller outer diameter than a tubular one, the rigidity of the linear member 20 can be increased, so that the outer diameter of the endoscopic treatment instrument 1 can be decreased while the insertability of the endoscopic treatment instrument 1 is improved.

The material forming the linear member 20 may be a conductive material and is preferably a metal wire material. If the linear member 20 is formed from a metal wire material, the linear member 20 can also have a role as a lead wire for supplying power to the conductive tip 30, so that it is not necessary to provide a lead wire in the inner cavity of the tubular member 10, and the outer diameter of the endoscopic treatment instrument 1 can be decreased.

Examples of the metal wire material forming the linear member 20 include stainless steel, 316L stainless steel, which is medical stainless steel, tantalum, Ni—Ti-based alloys, Fe—Mg—Si-based alloys, Co—Cr-based alloys, Co—Ni-based alloys, and carbon steel. Among them, the material forming the linear member 20 is preferably a stainless steel wire material. If the linear member 20 is formed from a stainless steel wire material, the linear member 20 can be produced at low cost, and the safety and stability of the linear member 20 can be improved.

The linear member 20 may be a single wire or a stranded wire obtained by twisting single wires. When the linear member 20 is a stranded wire, the flexibility of the linear member 20 can be increased. As a result, the endoscopic treatment instrument 1 can also become flexible, so that the insertability of the endoscopic treatment instrument 1 can be improved.

Although not shown, the linear member 20 may have a coating layer on the surface thereof. If the linear member 20 has a coating layer, it is possible to reduce the friction between the linear member 20 and the tubular member 10 to improve the slidability therebetween, so that it is easy to move the linear member 20 in the long axis direction in order to cause the conductive tip 30 to protrude or retract from or into the distal end 10d of the tubular member 10. Examples of the material of the coating layer of the linear member 20 include fluorine-based resins such as PTFE, PFA, ETFE, and tetrafluoroethylene propylene-hexafluoride copolymer (FEP). In addition, as for a method for forming the coating layer on the linear member 20, for example, the material forming the coating layer may be coated on the surface of the linear member 20, and a dipping method, a spray method, a fluidized bed method, a kneader coater method, or the like can be used.

The linear member 20 may be formed from one type of wire material, but is preferably formed from a plurality of members such as joining a plurality of wire materials in the middle in the long axis direction. Examples of a method for joining a plurality of wire materials in the middle include methods of crimping and coupling with a metal tube, welding, bonding, and press-fitting. If the linear member 20 is formed from a plurality of members, for example, the outer diameter of the wire material on the proximal side can be made larger than the outer diameters of the wire material on the distal side to increase the rigidity on the proximal side, so that it is possible to change the physical properties of the linear member 20, etc., in the long axis direction such as making it easier to efficiently transmit a force applied from the hand side of the endoscopic treatment instrument 1, to the tip side.

The conductive tip 30 is provided on the distal side of the linear member 20. In a state where a current is generated by power supplied from the hand side of the endoscopic treatment instrument 1, the conductive tip 30 is brought into contact with a lesion site to, for example, excise or cauterize the lesion site. The distal end of the conductive tip 30 can protrude or retract from or into the distal end 10d of the tubular member 10 by moving the linear member 20 in the long axis direction. As for the conductive tip 30, it is sufficient that at least a part of the conductive tip 30 can be disposed in the inner cavity of the tubular member 10. That is, it is sufficient that the proximal end 30p of the conductive tip 30 can be disposed in the inner cavity of the tubular member 10.

Examples of a method for fixing the conductive tip 30 and the linear member 20 to each other include methods of crimping and coupling with a metal tube, welding, bonding, and press-fitting. Among them, the conductive tip 30 and the linear member 20 are preferably fixed to each other by welding. If the conductive tip 30 and the linear member 20 are fixed to each other by welding, the conductive tip 30 and the linear member 20 can be firmly fixed to each other.

As shown in FIG. 2 to FIG. 4, the proximal end 30p of the conductive tip 30 is preferably located on the proximal side with respect to the distal end 20d of the linear member 20. If the proximal end 30p of the conductive tip 30 is located on the proximal side with respect to the distal end 20d of the linear member 20, the length by which the conductive tip 30 and the linear member 20 are in contact with each other can be increased in the long axis direction. As a result, the joining force between the conductive tip 30 and the linear member 20 can be increased. In order to locate the proximal end 30p of the conductive tip 30 on the proximal side with respect to the distal end 20d of the linear member 20, for example, a hole is provided on the proximal side of the conductive tip 30, and the distal end 20d of the linear member 20 is inserted and fixed in the hole. In addition, the proximal end 30p of the conductive tip 30 and the distal end 20d of the linear member 20 can be joined directly to each other, or the conductive tip 30 and the linear member 20 can be fixed to each other, for example, by disposing a fixing tube on the outer peripheries of the conductive tip 30 and the linear member 20.

Examples of the material forming the conductive tip 30 include stainless steel, 316L stainless steel, tantalum, Ni—Ti-based alloys, Fe—Mg—Si-based alloys, Co—Cr-based alloys, Co—Ni-based alloys, and carbon steel. Among them, the material forming the conductive tip 30 is preferably stainless steel. If the conductive tip 30 is formed from stainless steel, the conductive tip 30 can be produced at low cost, and the safety and stability of the conductive tip 30 can be improved.

The material forming the conductive tip 30 is preferably the same as the material forming the linear member 20. When the material forming the conductive tip 30 is the same as the material forming the linear member 20, it is possible to increase the fixing strength between the conductive tip 30 and the linear member 20, for example, by welding the conductive tip 30 and the linear member 20 to each other.

As shown in FIG. 2 to FIG. 4, the conductive tip 30 preferably has an enlarged portion 31 having a maximum outer diameter larger than the minimum inner diameter of the tubular member 10, on the proximal side of the conductive tip 30. The enlarged portion 31 is preferably disposed on the proximal side with respect to the portion that has the minimum inner diameter of the tubular member 10. If the conductive tip 30 has the enlarged portion 31, movement of the conductive tip 30 to the distal side can be restricted by the enlarged portion 31 coming into contact with the portion that has the minimum inner diameter of the tubular member 10. Therefore, it is possible to control the amount of protrusion of the conductive tip 30 from the distal end 10d of the tubular member 10 to an appropriate amount.

The enlarged portion 31 is preferably disposed at the proximal end 30p of the conductive tip 30. If the enlarged portion 31 is disposed at the proximal end 30p of the conductive tip 30, it is possible to efficiently restrict movement of the conductive tip 30 to the distal side, and the amount of protrusion of the conductive tip 30 can be controlled even when an excessive force is applied to the conductive tip 30 in the distal direction from the hand side through the linear member 20.

The outer diameter of the enlarged portion 31 is preferably not smaller than 1.5 times, more preferably not smaller than 1.7 times, and further preferably not smaller than 2 times the minimum inner diameter of the tubular member 10. If the lower limit of the ratio of the outer diameter of the enlarged portion 31 to the minimum inner diameter of the tubular member 10 is set to be in the above range, a sufficient contact area between the enlarged portion 31 and the tubular member 10 can be ensured. Therefore, it is easier to control the amount of protrusion of the conductive tip 30. In addition, the outer diameter of the enlarged portion 31 is preferably not larger than 5 times, more preferably not larger than 4 times, and further preferably not larger than 3 times the minimum inner diameter of the tubular member 10. If the upper limit of the ratio of the outer diameter of the enlarged portion 31 to the minimum inner diameter of the tubular member 10 is set to be in the above range, the outer diameter of the distal end portion of the endoscopic treatment instrument 1 can be prevented from being excessively increased, and the insertability of the endoscopic treatment instrument 1 into the forceps channel of the endoscope can be improved.

The linear member 20 is preferably fixed to the enlarged portion 31 of the conductive tip 30. If the linear member 20 is fixed to the enlarged portion 31, a sufficient contact area between the conductive tip 30 and the linear member 20 can be ensured, so that the joining strength between the conductive tip 30 and the linear member 20 can be increased to improve the durability.

The manipulation portion 40 is provided on the proximal side of the linear member 20. The manipulation portion 40 is disposed on the hand side of the endoscopic treatment instrument 1, and is a member to be held and manipulated by the user when the user operates the endoscopic treatment instrument 1.

As shown in FIG. 1, the manipulation portion 40 includes a manipulation portion body 50 and a slider 60. A proximal end portion of the tubular member 10 is fixed to the manipulation portion body 50. A proximal end portion of the linear member 20 is fixed to the slider 60, and the slider 60 is slidable relative to the manipulation portion body 50 in the long axis direction. The proximal end portion of the tubular member 10 and the manipulation portion body 50 may be fixed directly to each other, or may be fixed indirectly, for example, via a member. By moving the slider 60 from the proximal side to the distal side, it is possible to cause the conductive tip 30 to protrude from the tubular member 10. That is, by the user of the endoscopic treatment instrument 1 moving the slider 60 relative to the manipulation portion body 50 to the distal side, it is possible to cause the conductive tip 30 to protrude from the distal end 10d of the tubular member 10. By moving the slider 60 relative to the manipulation portion body 50 to the proximal side, it is possible to house at least a part on the proximal side of the conductive tip 30 in the inner cavity of the tubular member 10, so that the amount of protrusion of the conductive tip 30 can be adjusted.

The manipulation portion 40 has: a primary stop point where the manipulation portion body 50 and the slider 60 comes into contact with each other by relative movement of the manipulation portion body 50 and the slider 60; and a primary stop release point on the distal side with respect to the primary stop point.

Examples of the materials forming the manipulation portion body 50 and the slider 60 include synthetic resins including: polyolefin-based resins such as polyethylene and polypropylene; polyester-based resins such as polyethylene terephthalate (PET); polycarbonate-based resins; ABS-based resins; and polyurethane-based resins. Among them, the material forming at least either one of the manipulation portion body 50 and the slider 60 is preferably an ABS resin. If the material forming at least either one of the manipulation portion body 50 and the slider 60 is an ABS resin, the strength of the manipulation portion 40 can be increased, so that the endoscopic treatment instrument 1 can have high durability. The material forming the manipulation portion body 50 and the material forming the slider 60 may be the same or different from each other.

The endoscopic treatment instrument 1 satisfies the following [Condition 1] and [Condition 2].

[Condition 1]

In a state where the conductive tip 30 is not provided to the linear member 20,
- (1) by moving the slider 60 relative to the manipulation portion body 50 toward the distal side, at least a part of the slider 60 comes into contact with at least a part of the manipulation portion body 50 at the primary stop point located in the movable range of the slider 60, whereby the movement of the slider 60 in the distal direction is stopped,
- (2) the slider 60 is moved from the primary stop point in the distal direction by applying a pushing force equal to or greater than a predetermined force to the slider 60, and
- (3) at the primary stop release point located in the movable range of the slider 60, the slider 60 can be moved in the distal direction even when a pushing force applied to the slider 60 is less than the predetermined force.

[Condition 2]

In a state where the conductive tip 30 is provided to the linear member 20,
when the slider 60 is at the primary stop point, or when the slider 60 is at the primary stop release point, a distal end portion of the conductive tip 30 is located at a first position P1 located on the distal side with respect to the distal end 10d of the tubular member 10.

FIG. 2(a) shows a cross-sectional view including the long axis of the manipulation portion 40 in a state where the slider 60 is at the primary stop point. As shown in FIG. 2(a), in a state where the conductive tip 30 is not provided to the linear member 20, by moving the slider 60 relative to the manipulation portion body 50 toward the distal side, at least a part of the slider 60 comes into contact with at least a part of the manipulation portion body 50 at the primary stop point, which is located in the movable range of the slider 60, to stop the movement of the slider 60 in the distal direction {(1) of [Condition 1]}.

In a state where the conductive tip 30 is not provided to the linear member 20, and when the slider 60 is located at the primary stop point, by applying a pushing force equal to or greater than the predetermined force to the slider 60, the slider 60 is moved from the primary stop point in the distal direction {(2) of [Condition 1]}.

FIG. 3(a) shows a cross-sectional view including the long axis of the manipulation portion 40 in a state where the slider 60 is at the primary stop release point. As shown in FIG. 3(a), in a state where the conductive tip 30 is not provided to the linear member 20, at the primary stop release point located in the movable range of the slider 60, the slider 60 can be moved in the distal direction even when a pushing force applied to the slider 60 is less than the predetermined force {(3) of [Condition 1]}.

That is, in the endoscopic treatment instrument 1, in a state where the conductive tip 30 is not provided to the linear member 20 and the slider 60 is on the proximal side with respect to the primary stop point, the slider 60 is located at the primary stop point by applying a pushing force less than the predetermined force to the slider 60 in the distal direction relative to the manipulation portion body 50. In a state where the slider 60 is located at the primary stop point, by applying a pushing force equal to or greater than the predetermined force to the slider 60 in the distal direction, the slider 60 is moved to the distal side with respect to the primary stop point to be located at the primary stop release point. In a state where the slider 60 is located at the primary stop release point, the slider 60 can be returned from the primary stop release point to the primary stop point by applying a force equal to or greater than the predetermined force to the slider 60 in the proximal side.

FIG. 2(*b*) shows a cross-sectional view including the long axis of the distal end portion of the endoscopic treatment instrument 1 in a state where the slider 60 is at the primary stop point, and FIG. 3(*b*) shows a cross-sectional view including the long axis of the distal end portion of the endoscopic treatment instrument 1 in a state where the slider 60 is at the primary stop release point. As shown in FIG. 2(*b*) and FIG. 3(*b*), in a state where the conductive tip 30 is provided to the linear member 20, when the slider 60 is at the primary stop point, or when the slider 60 is at the primary stop release point, the distal end portion of the conductive tip 30 is located at the first position P1, which is located on the distal side with respect to the distal end 10*d* of the tubular member 10 ([Condition 2]).

Specifically, in the case where the conductive tip 30 is provided to the linear member 20, when the slider 60 is located at the primary stop point, the distal end portion of the conductive tip 30 is located at the first position P1 as shown in FIG. 2(*b*). In addition, in the case where the conductive tip 30 is provided to the linear member 20, when the slider 60 is located at the primary stop release point as well, the distal end portion of the conductive tip 30 is located at the first position P1 as shown in FIG. 3(*b*). If the distance by which the slider 60 is moved from the primary stop point to the primary stop release point is absorbed by a component included in the endoscopic treatment instrument 1 such as the linear member 20 or the conductive tip 30, the distal end portion of the conductive tip 30 can be located at the first position P1 both when the slider 60 is located at the primary stop point and when the slider 60 is located at the primary stop release point.

Specific examples for absorbing the distance, by which the slider 60 is moved from the primary stop point to the primary stop release point, by the component included in the endoscopic treatment instrument 1 include: forming the linear member 20 so as to have elasticity and sagging the linear member 20; and incorporating a component capable of shortening the length in the long axis direction such as a spring, into at least either one of the linear member 20 and the conductive tip 30. Among them, by using the linear member 20 having elasticity and sagging the linear member 20, the distance by which the slider 60 is moved from the primary stop point to the primary stop release point is preferably absorbed. By absorbing the distance, by which the slider 60 is moved from the primary stop point to the primary stop release point, by sagging the linear member 20, the number of components included in the endoscopic treatment instrument 1 can be reduced to simplify the configuration of the endoscopic treatment instrument 1. Thus, the durability of the endoscopic treatment instrument 1 can be increased, and the production cost of the endoscopic treatment instrument 1 can be reduced.

If the endoscopic treatment instrument 1 satisfies [Condition 1] and [Condition 2], it can be easier to maintain a state where the conductive tip 30 protrudes from the distal end 10*d* of the tubular member 10 by a certain amount. In addition, the fact that the slider 60 is located at the primary stop release point by applying a pushing force equal to or greater than the predetermined force to the slider 60 when the slider 60 is located at the primary stop point, means that, in a state where the slider 60 is located at the primary stop release point, the distal end portion of the conductive tip 30 is not moved to the proximal side with respect to the first position P1 unless a force equal to or greater than the predetermined force is applied to the slider 60 in the proximal side. Therefore, a state where the conductive tip 30, which is a treatment tool, protrudes can be maintained, and can be prevented from being unintentionally released. That is, in a state where the distal end portion of the conductive tip 30 is located at the first position P1, when the conductive tip 30 is pushed to the proximal side due to contact of another object with the conductive tip 30 or the like, the amount of protrusion of the conductive tip 30 can be prevented from being unintentionally decreased by the user, or the conductive tip 30 can be prevented from being housed in the inner cavity of the tubular member 10. Moreover, it is possible for the user to perform a manipulation for decreasing the amount of protrusion of the conductive tip 30 or a manipulation for housing the conductive tip 30 in the inner cavity of the tubular member 10, by pulling the slider 60 and applying a force equal to or greater than the predetermined force to the slider 60 in the proximal side.

The stop of the slider 60 at the primary stop point signals that the distal end portion of the conductive tip 30 is located at the first position P1, which is located on the distal side with respect to the distal end 10*d* of the tubular member 10. For example, if a position at which the amount of protrusion of the conductive tip 30 is suitable for incising a lesion site is set as the first position P1, it can be sensed that the amount of protrusion of the conductive tip 30 becomes suitable for incising a lesion site, by the slider 60 located on the proximal side with respect to the primary stop point being moved toward the distal side and reaching the primary stop point to stop the movement of the slider 60 in the distal direction. In addition, by obtaining a state where the movement of the slider 60 in the distal direction is not stopped and the slider 60 is on the proximal side with respect to the primary stop point, it can be sensed that the amount of protrusion of the conductive tip 30 is smaller than an appropriate amount suitable for incising a lesion site, so that it is also possible to perform a procedure such as scraping off the surface of a tissue, such as a lesion site, in a shallower manner.

FIG. 4(*a*) shows a cross-sectional view including the long axis of the manipulation portion 40 in a state where the slider 60 is at a secondary stop point. As shown in FIG. 4(*a*), preferably, the manipulation portion 40 further has a secondary stop point where the manipulation portion body 50 and the slider 60 come into contact with each other by relative movement of the manipulation portion body 50 and the slider 60, the secondary stop point is located on the proximal side in the movable range of the slider 60 with respect to the primary stop point, and in a state where the conductive tip 30 is not provided to the slider 60, by pulling the slider 60 toward the proximal side, at least a part of the slider 60 comes into contact with at least a part of the manipulation portion body 50 at the secondary stop point to stop the movement of the slider 60 in the proximal direction. If the endoscopic treatment instrument 1 has the secondary stop point at which the movement of the slider 60 in the proximal direction is stopped, when the conductive tip 30 is housed in the inner cavity of the tubular member 10, or when the amount of protrusion of the conductive tip 30 is small, the distance between a distal end 30*d* of the conductive tip 30 and the distal end 10*d* of the tubular member 10 can be prevented from being excessively increased. Therefore, it is possible to quickly increase the amount of protrusion of the conductive tip 30 to an amount of protrusion suitable for incising a lesion site, and a procedure can be performed quickly.

The distance from the primary stop point to the secondary stop point is preferably larger than the distance from the primary stop point to the primary stop release point. If the distance from the primary stop point to the secondary stop point is larger than the distance from the primary stop point to the primary stop release point, the range of movement of the slider 60 to the proximal side can be increased. Therefore, the range of movement of the conductive tip 30 to the proximal side can also be increased, so that it can be easier to perform adjustment for decreasing the amount of protrusion of the conductive tip 30 from the distal end 10d of the tubular member 10.

The distance from the primary stop point to the secondary stop point is preferably not smaller than 2 times, more preferably not smaller than 3 times, and further preferably not smaller than 5 times the distance from the primary stop point to the primary stop release point. If the lower limit of the ratio of the distance from the primary stop point to the secondary stop point to the distance from the primary stop point to the primary stop release point is set to be in the above range, the range of movement of the conductive tip 30 to the proximal side for decreasing the amount of protrusion of the conductive tip 30 can be sufficiently larger than the range of movement of the conductive tip 30 to the distal side for causing the conductive tip 30 to protrude from the distal end 10d of the tubular member 10. As a result, it is easier to adjust the amount of protrusion of the conductive tip 30. In addition, the distance from the primary stop point to the secondary stop point is preferably not larger than 20 times, more preferably not larger than 15 times, and further preferably not larger than 10 times the distance from the primary stop point to the primary stop release point. If the upper limit of the ratio of the distance from the primary stop point to the secondary stop point to the distance from the primary stop point to the primary stop release point is set to be in the above range, the range of movement of the conductive tip 30 to the proximal side is less likely to be increased, and an increase in the size of the manipulation portion 40 can be prevented. Therefore, the manipulability of the endoscopic treatment instrument 1 can be improved.

FIG. 4(b) shows a cross-sectional view including the long axis of the distal end portion of the endoscopic treatment instrument 1 in a state where the slider 60 is at the secondary stop point. In a state where the conductive tip 30 is provided to the linear member 20, when the slider 60 is located at the secondary stop point, the distal end 30d of the conductive tip 30 may be located on the distal side with respect to the distal end 10d of the tubular member 10. However, as shown in FIG. 4(b), when the slider 60 is located at the secondary stop point, the distal end 30d of the conductive tip 30 is preferably located on the proximal side with respect to the distal end 10d of the tubular member 10. If the distal end 30d of the conductive tip 30 is located on the proximal side with respect to the distal end 10d of the tubular member 10 when the slider 60 is located at the secondary stop point in a state where the conductive tip 30 is provided to the linear member 20, the entirety of the conductive tip 30 can be housed in the inner cavity of the tubular member 10 by pulling the slider 60 toward the proximal side to locate the slider 60 at the secondary stop point. Therefore, while the endoscopic treatment instrument 1 is transferred from the forceps port of the endoscope through the forceps channel of the endoscope to a region to be treated in which a lesion site is located, the conductive tip 30 can be prevented from damaging the forceps port and the inside of the forceps channel of the endoscope, and internal tissues other than the region to be treated.

In a state where the conductive tip 30 is provided to the linear member 20, when the slider 60 is on the proximal side with respect to the primary stop point, the distal end 30d of the conductive tip 30 is preferably located on the proximal side with respect to the first position P1. If the distal end 30d of the conductive tip 30 is located on the proximal side with respect to the first position P1 when the slider 60 is located on the proximal side with respect to the primary stop point, it is possible to decrease the amount of protrusion of the conductive tip 30 from the distal end 10d of the tubular member 10 more than when the distal end portion of the conductive tip 30 is located at the first position P1. As a result, the amount of protrusion of the conductive tip 30 can be adjusted in accordance with the state of a lesion site or the like, and the endoscopic treatment instrument 1 can be an instrument with which a procedure is easily performed.

The manipulation portion body 50 and the slider 60 have contact portions such as projections and recesses on surfaces where the manipulation portion body 50 and the slider 60 face each other, and it is possible to stop movement of the slider 60 at the primary stop point or the secondary stop point by these contact portions coming into contact with each other. That is, the manipulation portion body 50 has a contact portion on the surface facing the slider 60, and the slider 60 has a contact portion on the surface facing the manipulation portion body 50. By the contact portion of the manipulation portion body 50 and the contact portion of the slider 60 coming into contact with each other, movement of the slider 60 to the distal direction is stopped at the primary stop point, and movement of the slider 60 to the proximal direction is stopped at the secondary stop point.

As shown in FIG. 2 to FIG. 4, preferably, the manipulation portion body 50 has a manipulation portion body side projection 51 on the surface facing the slider 60, the slider 60 has a slider side projection 61 on the surface facing the manipulation portion body 50, and contact between at least a part of the slider 60 and at least a part of the manipulation portion body 50 is contact between the manipulation portion body side projection 51 and the slider side projection 61. If the contact between at least a part of the slider 60 and at least a part of the manipulation portion body 50 is the contact between the manipulation portion body side projection 51 and the slider side projection 61, movement of the slider 60 can be reliably stopped by the contact between the manipulation portion body side projection 51 and the slider side projection 61 while the structures of the manipulation portion body 50 and the slider 60 are simplified.

The manipulation portion body 50 may have only one manipulation portion body side projection 51, or may have a plurality of manipulation portion body side projections 51. In addition, the slider 60 may have only one slider side projection 61, or may have a plurality of slider side projections 61. Among them, as shown in FIG. 2 to FIG. 4, preferably, the manipulation portion body 50 has a plurality of manipulation portion body side projections 51, and the slider 60 has one slider side projection 61. If the manipulation portion body 50 has a plurality of manipulation portion body side projections 51, it is possible to stop movement of the slider 60 at a plurality of points. In addition, if the slider 60 has one slider side projection 61, when moving the slider 60 in the long axis direction, it is possible to minimize the frictional force generated between the slider side projection 61 and the manipulation portion body 50 and smoothly move the slider 60.

FIG. 5 shows a cross-sectional view including the long axis of the manipulation portion 40 in a state where the slider 60 is at the primary stop point in another embodiment of the present invention. In the manipulation portion 40, as shown in FIG. 2 to FIG. 4, preferably, the manipulation portion body 50 has a plurality of manipulation portion body side projections 51, and the slider 60 has one slider side projection 61. However, as shown in FIG. 5, the manipulation portion body 50 may have one manipulation portion body side projection 51, and the slider 60 may have a plurality of slider side projections 61.

Next, a second endoscopic treatment instrument according to an embodiment of the present invention will be described. In the following description, the description of the part that overlaps with the above description will be omitted.

FIG. 6(a) shows a cross-sectional view including the long axis of the manipulation portion 40 in a state where the manipulation portion body side projection 51 and the slider side projection 61 are spaced apart from each other by a distance equal to or larger than a predetermined distance, FIG. 6(b) shows a cross-sectional view including the long axis of the distal end portion of the endoscopic treatment instrument 1 in a state where the manipulation portion body side projection 51 and the slider side projection 61 are spaced apart from each other by the distance equal to or larger than the predetermined distance, FIG. 7(a) shows a cross-sectional view including the long axis of the manipulation portion 40 in a state where the manipulation portion body side projection 51 and the slider side projection 61 are spaced apart from each other by a distance less than the predetermined distance, FIG. 7(b) shows a cross-sectional view including the long axis of the distal end portion of the endoscopic treatment instrument 1 in a state where the manipulation portion body side projection 51 and the slider side projection 61 are spaced apart from each other by the distance less than the predetermined distance, FIG. 8(a) shows a cross-sectional view including the long axis of the manipulation portion 40 in a state where the manipulation portion body side projection 51 and the slider side projection 61 are in contact with each other, and FIG. 8(b) shows a cross-sectional view including the long axis of the distal end portion of the endoscopic treatment instrument 1 in a state where the manipulation portion body side projection 51 and the slider side projection 61 are in contact with each other.

As shown in FIG. 6 to FIG. 8, the conductive tip 30 has an enlarged portion 31 having a maximum outer diameter larger than the minimum inner diameter of the tubular member 10, on the proximal side of the conductive tip 30, and the tubular member 10 has a contact portion 12 which comes into contact with a distal end 31d of the enlarged portion 31, the manipulation portion body 50 has a manipulation portion body side projection 51, and the slider 60 has a slider side projection 61.

When the slider side projection 61 is located on the proximal side with respect to the manipulation portion body side projection 51 and the manipulation portion body side projection 51 and the slider side projection 61 are spaced apart from each other by the distance equal to or larger than the predetermined distance as shown in FIG. 6(a), the enlarged portion 31 and the contact portion 12 are not in contact with each other as shown in FIG. 6(b).

When the slider side projection 61 is located on the proximal side with respect to the manipulation portion body side projection 51 and the manipulation portion body side projection 51 and the slider side projection 61 are spaced apart from each other by the predetermined distance as shown in FIG. 7(a), the enlarged portion 31 and the contact portion 12 are in contact with each other as shown in FIG. 7(b).

When the slider side projection 61 is located on the proximal side with respect to the manipulation portion body side projection 51 and the manipulation portion body side projection 51 and the slider side projection 61 are in contact with each other as shown in FIG. 8(a), the enlarged portion 31 and the contact portion 12 are in contact with each other as shown in FIG. 8(b).

That is, when the distance D1 between the manipulation portion body side projection 51 and the slider side projection 61 is equal to or larger than the predetermined distance as shown in FIG. 6, the enlarged portion 31 and the contact portion 12 are not in contact with each other, and, by applying, to the slider 60 in this state, a force toward the distal side to move the slider 60 in the distal direction, the enlarged portion 31 and the contact portion 12 are brought into contact with each other as shown in FIG. 7, but the manipulation portion body side projection 51 and the slider side projection 61 are spaced apart from each other by a distance less than the predetermined distance, so that the manipulation portion body side projection 51 and the slider side projection 61 are not in contact with each other. In other words, before the manipulation portion body side projection 51 and the slider side projection 61 come into contact with each other, the enlarged portion 31 and the contact portion 12 come into contact with each other and the amount of protrusion of the conductive tip 30 is maximized. Then, when a force toward the distal side is further applied to the slider 60 in the state shown in FIG. 7 to move the slider 60 in the distal direction, the manipulation portion body side projection 51 and the slider side projection 61 also come into contact with each other with the enlarged portion 31 and the contact portion 12 being in contact with each other as shown in FIG. 8.

When the manipulation portion body side projection 51 and the slider side projection 61 are spaced apart from each other by a distance equal to or larger than the predetermined distance, the enlarged portion 31 and the contact portion 12 are not in contact with each other. When the manipulation portion body side projection 51 and the slider side projection 61 are spaced apart from each other by a distance less than the predetermined distance, the enlarged portion 31 and the contact portion 12 are in contact with each other. When the manipulation portion body side projection 51 and the slider side projection 61 are in contact with each other, since the enlarged portion 31 and the contact portion 12 are in contact with each other, the amount of protrusion of the conductive tip 30 is maximized before the slider 60 is moved in the distal direction to bring the manipulation portion body side projection 51 and the slider side projection 61 into contact with each other. Thus, even in a state where the linear member 20 is sagged, such as when the tubular member 10 is bent, it is possible to cause the conductive tip 30 to protrude up to the maximum amount of protrusion, so that it can be easier to incise a lesion site. In addition, after the enlarged portion 31 and the contact portion 12 come into contact with each other and the amount of protrusion of the conductive tip 30 is maximized, a force is further applied to the slider 60 in the distal direction in order to bring the manipulation portion body side projection 51 and the slider side projection 61 into contact with each other. Thus, even when a force toward the proximal side is applied due to contact of another object with the distal end 30d of the conductive tip 30 or the like, the conductive tip 30 is less likely to retreat to the proximal side, and the amount of protrusion of the conductive tip 30 can be prevented from being unintentionally decreased by the user of the endoscopic treatment instrument 1, or the conductive tip 30 can be prevented from being housed in the inner cavity of the tubular member 10. That is, a state where the conductive tip 30, which is a treatment tool, protrudes can be maintained, and the conductive tip 30 can be prevented from unintentionally retreating into the tubular member.

FIG. 9(a) shows a cross-sectional view including the long axis of the manipulation portion 40 in a state where the slider side projection 61 is located on the distal side with respect to the manipulation portion body side projection 51, and FIG. 9(b) shows a cross-sectional view including the long axis of the distal end portion of the endoscopic treatment instrument 1 in a state where the slider side projection 61 is located on the distal side with respect to the manipulation portion body side projection 51. When the slider side projection 61 is located on the distal side with respect to the manipulation portion body side projection 51 as shown in FIG. 9(a), the enlarged portion 31 and the contact portion 12 are preferably in contact with each other as shown in FIG. 9(b). If the enlarged portion 31 and the contact portion 12 are in contact with each other when the slider side projection 61 is located on the distal side with respect to the manipulation portion body side projection 51, in a state where the amount of protrusion of the conductive tip 30 is maximized, the movement of the slider 60 in the proximal side is hindered, so that the conductive tip 30 is less likely to retreat to the proximal side even when a force is applied to the distal end 30d of the conductive tip 30 in the proximal direction. Furthermore, if the enlarged portion 31 and the contact portion 12 are in contact with each other when the slider side projection 61 is located on the distal side with respect to the manipulation portion body side projection 51, it is possible to maximize the amount of protrusion of the conductive tip 30 even when a force is not continuously applied to the slider 60 in the distal direction.

Preferably, as shown in FIG. 8, the distal end portion of the conductive tip 30 is located at the first position P1, which is located on the distal side with respect to the distal end 10d of the tubular member 10, in a state where the distal side surface of the manipulation portion body side projection 51 and the proximal side surface of the slider side projection 61 are in contact with each other, and, as shown in FIG. 9, the distal end portion of the conductive tip 30 is located at the first position P1 in a state where the proximal side surface of the manipulation portion body side projection 51 and the distal side surface of the slider side projection 61 are in contact with each other. That is, the slider 60 is moved in the long axis direction in order to make a shift from a state where the distal side surface of the manipulation portion body side projection 51 and the proximal side surface of the slider side projection 61 are in contact with each other to a state where the proximal side surface of the manipulation portion body side projection 51 and the distal side surface of the slider side projection 61 are in contact with each other, but the position of the distal end portion of the conductive tip 30 is preferably maintained at the first position P1 even when the slider 60 is moved in the long axis direction. If the distal end portion of the conductive tip 30 is located at the first position P1 in a state where the distal side surface of the manipulation portion body side projection 51 and the proximal side surface of the slider side projection 61 are in contact with each other, and the distal end portion of the conductive tip 30 is located at the first position P1 even in a state where the proximal side surface of the manipulation portion body side projection 51 and the distal side surface of the slider side projection 61 are in contact with each other, after the distal side surface of the manipulation portion body side projection 51 and the proximal side surface of the slider side projection 61 come into contact with each other and the distal end portion of the conductive tip 30 is located at the first position P1, a force is further applied to the slider 60 in the distal direction in order to bring the proximal side surface of the manipulation portion body side projection 51 and the distal side surface of the slider side projection 61 into contact with each other. Therefore, the conductive tip 30 is less likely to retreat to the proximal side when a force is applied in the proximal direction to the distal end portion of the conductive tip 30 located at the first position P1, and the amount of protrusion of the conductive tip 30 can be prevented from being unintentionally decreased by the user, or the conductive tip 30 can be prevented from being housed in the inner cavity of the tubular member 10.

In order to locate the distal end portion of the conductive tip 30 at the first position P1 both in a state where the distal side surface of the manipulation portion body side projection 51 and the proximal side surface of the slider side projection 61 are in contact with each other and in a state where the proximal side surface of the manipulation portion body side projection 51 and the distal side surface of the slider side projection 61 are in contact with each other, the distance by which the slider 60 is moved from a state where the distal side surface of the manipulation portion body side projection 51 and the proximal side surface of the slider side projection 61 are in contact with each other to a state where the proximal side surface of the manipulation portion body side projection 51 and the distal side surface of the slider side projection 61 are in contact with each other, is absorbed by the component included in the endoscopic treatment instrument 1 such as the linear member 20 or the conductive tip 30, whereby it is possible to locate the distal end portion of the conductive tip 30 at the first position P1 both in a state where the distal side surface of the manipulation portion body side projection 51 and the proximal side surface of the slider side projection 61 are in contact with each other and in a state where the proximal side surface of the manipulation portion body side projection 51 and the distal side surface of the slider side projection 61 are in contact with each other.

Although not shown, at least either one of the linear member 20 and the conductive tip 30 preferably has a length absorption portion which shortens the length in the long axis direction of at least either one of the linear member 20 and the conductive tip 30 when a force is applied from the proximal side toward the distal side. That is, in the case where the linear member 20 has a length absorption portion, when a force is applied to the linear member 20 in the distal direction, the length absorption portion absorbs the length in the long axis direction of the linear member 20. In the case where the conductive tip 30 has a length absorption portion, when a force is applied to the conductive tip 30 in the distal direction, the length absorption portion absorbs the length in the long axis direction of the conductive tip 30. If at least either one of the linear member 20 and the conductive tip 30 has a length absorption portion, when a force is applied to the distal end 30d of the conductive tip 30 in the proximal direction in a state where the conductive tip 30 protrudes from the distal end 10d of the tubular member 10, the amount of protrusion of the conductive tip 30 is less likely to be decreased, and the conductive tip 30 is less likely to be housed in the inner cavity of the tubular member 10.

Examples of the length absorption portion include a spring which can compress the length in the long axis direction thereof and return the length to the original length, and a resin member having elasticity. Among them, the length absorption portion is preferably a spring. If a spring is used as the length absorption portion, the length absorption portion is less likely to be broken even when a process, in which the length in the long axis direction of the length absorption portion is compressed due to a force being applied in the distal direction to at least either one of the linear member 20 and the conductive tip 30 having the length absorption portion and is returned to the original length due to disappearance of the force applied in the distal direction to at least either one of the linear member 20 and the conductive tip 30 having the length absorption portion, is repeated. Thus, the durability of the endoscopic treatment instrument 1 can be increased.

When the slider 60 is moved to the most proximal position in the movable range thereof, the distal end 30d of the conductive tip 30 may be located on the distal side with respect to the distal end 10d of the tubular member 10, or may be located on the proximal side with respect to the distal end 10d of the tubular member 10. If the distal end 30d of the conductive tip 30 is located on the distal side with respect to the distal end 10d of the tubular member 10 when the slider 60 is moved to the most proximal position in the movable range thereof, it is easy to mark a necessary location by cauterizing body tissues very shallowly. In this case, the distal portion of the conductive tip 30 that protrudes from the distal end 10d of the tubular member 10 is preferably as small as about 0.2 mm to 1.0 mm. If the distal end 30d of the conductive tip 30 is located on the distal side with respect to the distal end 10d of the tubular member 10, the distal end portion of the conductive tip 30 is constantly exposed from the tubular member 10. Therefore, a lesion site can be incised quickly, so that it is possible to shorten the time required for such a procedure.

The force required for moving the slider side projection 61 from the distal side of the manipulation portion body side projection 51 to the proximal side is preferably larger than the force required for moving the slider side projection 61 from the proximal side of the manipulation portion body side projection 51 to the distal side. If the force required for moving the slider side projection 61 from the distal side of the manipulation portion body side projection 51 to the proximal side is larger than the force required for moving the slider side projection 61 from the proximal side of the manipulation portion body side projection 51 to the distal side, the force required for moving the slider 60 in the proximal direction to decrease the amount of protrusion of the conductive tip 30 or for housing the conductive tip 30 in the inner cavity of the tubular member 10 is larger than the force required for moving the slider 60 in the distal direction to cause the conductive tip 30 to protrude. Therefore, even when a force is unintentionally applied to the conductive tip 30 in the proximal direction due to contact of another object with the conductive tip 30 or the like, the amount of protrusion of the conductive tip 30 can be prevented from being decreased, or the conductive tip 30 can be prevented from being housed in the tubular member 10.

In order to make the force required for moving the slider side projection 61 from the distal side of the manipulation portion body side projection 51 to the proximal side larger than the force required for moving the slider side projection 61 from the proximal side of the manipulation portion body side projection 51 to the distal side, for example, the slider side projection 61 is formed so as to have a tapered portion on the distal side surface thereof and have no tapered portion on the proximal side surface thereof, the coefficient of friction of the proximal side surface of the slider side projection 61 is increased, the manipulation portion body side projection 51 is formed so as to have a tapered portion on the proximal side surface thereof and have no tapered portion on the distal side surface thereof, or the coefficient of friction of the distal side surface of the manipulation portion body side projection 51 is increased.

Preferably, the slider side projection 61 has a tapered portion on the distal side surface thereof and has no tapered portion on the proximal side surface thereof, and the manipulation portion body side projection 51 has a tapered portion on the proximal side surface thereof and has no tapered portion on the distal side surface thereof. If the manipulation portion body side projection 51 has a tapered portion on the proximal side surface thereof and the slider side projection 61 has a tapered portion on the distal side surface thereof, when the slider side projection 61 is located on the proximal side with respect to the manipulation portion body side projection 51, it is easier to move the slider side projection 61 to the distal side beyond the manipulation portion body side projection 51, so that it can be easier to cause the conductive tip 30 to protrude from the tubular member 10. In addition, if the manipulation portion body side projection 51 has no tapered portion on the distal side surface thereof and the slider side projection 61 has no tapered portion on the proximal side surface thereof, when the slider side projection 61 is located on the distal side with respect to the manipulation portion body side projection 51, the force required for moving the slider side projection 61 in the proximal side beyond the manipulation portion body side projection 51 is larger than the force required for moving the slider side projection 61 to the distal side beyond the manipulation portion body side projection 51, so that the amount of protrusion of the conductive tip 30 can be prevented from being unintentionally decreased by the user, or the conductive tip 30 can be prevented from being housed in the tubular member 10.

The force required for moving the slider side projection 61 from the distal side of the manipulation portion body side projection 51 to the proximal side is preferably not smaller than 1.1 times, more preferably not smaller than 1.2 times, and further preferably not smaller than 1.3 times the force required for moving the slider side projection 61 from the proximal side of the manipulation portion body side projection 51 to the distal side. If the lower limit of the ratio of the force required for moving the slider side projection 61 to the proximal side to the force required for moving the slider side projection 61 to the distal side is set to be in the above range, the force required for moving the slider side projection 61 from the distal side of the manipulation portion body side projection 51 to the proximal side can be sufficiently larger than the force required for moving the slider side projection 61 from the proximal side of the manipulation portion body side projection 51 to the distal side. Therefore, when a force is applied to the distal end portion of the conductive tip 30 in the proximal direction, the amount of protrusion of the conductive tip 30 can be prevented from being decreased, or the conductive tip 30 can be prevented from being housed in the inner cavity of the tubular member 10. In addition, the force required for moving the slider side projection 61 from the distal side of the manipulation portion body side projection 51 to the proximal side is preferably not greater than 3 times, more preferably not greater than 2.5 times, and further preferably not greater than 2 times the force required for moving the slider side projection 61 from the proximal side of the manipulation portion body side projection 51 to the distal side. If the upper limit of the ratio of the force required for moving the slider side projection 61 to the proximal side to the force required for moving the slider side projection 61 to the distal side is set to be in the above range, it is easier to move the slider 60 to the proximal side when the user performs a manipulation for decreasing the amount of protrusion of the conductive tip 30 or a manipulation for housing the conductive tip 30 in the inner cavity of the tubular member 10.

Preferably, the manipulation portion body 50 has no projection on the proximal side with respect to the manipulation portion body side projection 51. If the manipulation portion body 50 has no projection on the proximal side with respect to the manipulation portion body side projection 51, it is easier to perform a manipulation for moving the slider 60 to the proximal side in a state where the slider side projection 61 is on the proximal side with respect to the manipulation portion body side projection 51. Therefore, in the case where it is necessary to decrease the amount of protrusion of the conductive tip 30 or house the conductive tip 30 in the inner cavity of the tubular member 10, it is easier to move the slider 60 to the proximal side.

As shown in FIG. 6 to FIG. 9, the conductive tip 30 preferably has an end portion 32 having a maximum outer diameter larger than the minimum inner diameter of the tubular member 10, at the distal end thereof. If the conductive tip 30 has the end portion 32, a situation in which the entirety of the conductive tip 30 is housed in the inner cavity of the tubular member 10 to make it impossible to incise the tissue at a lesion site, for example, when the distal end of the conductive tip 30 is pressed against the lesion site, can be prevented, and the procedure can be smoothly performed.

The maximum outer diameter of the end portion 32 is preferably not smaller than 1.1 times, more preferably not smaller than 1.3 times, and further preferably not smaller than 1.5 times the minimum inner diameter of the tubular member 10. If the lower limit of the ratio of the maximum outer diameter of the end portion 32 to the minimum inner diameter of the tubular member 10 is set to be in the above range, a sufficient area where the end portion 32 and the portion that has the minimum inner diameter of the tubular member 10 are in contact with each other can be ensured. Therefore, even when a strong force toward the proximal side is applied to the distal end of the conductive tip 30, the conductive tip 30 can be exposed from the distal end 10*d* of the tubular member 10. In addition, the maximum outer diameter of the end portion 32 is preferably not larger than 3.5 times, more preferably not larger than 3 times, and further preferably not larger than 2.5 times the minimum inner diameter of the tubular member 10. If the upper limit of the ratio of the maximum outer diameter of the end portion 32 to the minimum inner diameter of the tubular member 10 is set to be in the above range, the outer diameter of the end portion 32 is prevented from being excessively increased, and it is easier to precisely control where to incise the tissue at a lesion site.

DESCRIPTION OF REFERENCE SIGNS

1 endoscopic treatment instrument
10 tubular member
10*d* distal end of the tubular member
12 contact portion
20 linear member
20*d* distal end of the linear member
30 conductive tip
30*p* proximal end of the conductive tip
30*d* distal end of the conductive tip
31 enlarged portion
31*d* distal end of the enlarged portion
32 end portion
40 manipulation portion
50 manipulation portion body
51 manipulation portion body side projection
60 slider
61 slider side projection
P1 first position
D1 distance between the manipulation portion body side projection and the slider side projection

The invention claimed is:

1. An endoscopic treatment instrument comprising:
a tubular member having a distal end and a proximal end and having an inner cavity extending in a long axis direction thereof;
a linear member having a distal end and a proximal end, extending in the long axis direction, and disposed in the inner cavity of the tubular member;
a conductive tip provided on a distal side of the linear member; and
a manipulation portion provided on a proximal side of the linear member, wherein
the manipulation portion has a manipulation portion body to which a proximal end portion of the tubular member is fixed, a slider to which a proximal end portion of the linear member is fixed and which is disposed in the manipulation portion body and slidable relative to the manipulation portion body in the long axis direction, a primary stop point where the manipulation portion body and the slider come into contact with each other by relative movement of the manipulation portion body and the slider, and a primary stop release point on the distal side with respect to the primary stop point,
the conductive tip is configured to protrude from the tubular member by moving the slider from the proximal side to the distal side, and
the manipulation portion body and the slider are configured to satisfy the following [Condition 1] and [Condition 2]:
[Condition 1]
in a state where the conductive tip is not provided to the linear member by removing the conductive tip from the linear member, and the endoscopic treatment instrument is configured to satisfy the following (1) to (3),
(1) by moving the slider relative to the manipulation portion body toward the distal side, at least a part of the slider comes into contact with at least a part of the manipulation portion body at the primary stop point located in a movable range of the slider, whereby movement of the slider in a distal direction is stopped,
(2) the slider is moved from the primary stop point in the distal direction by applying a pushing force equal to or larger than a predetermined force to the slider, and
(3) at the primary stop release point located in the movable range of the slider, the slider can be moved in the distal direction even when a pushing force applied to the slider is less than the predetermined force; and
[Condition 2]
when the slider is at the primary stop point, or when the slider is at the primary stop release point, a distal end portion of the conductive tip is located at a first position located on the distal side with respect to the distal end of the tubular member.

2. The endoscopic treatment instrument according to claim 1, wherein
the manipulation portion further has a secondary stop point, and
the manipulation portion and the slider are configured such that i) the manipulation portion body and the slider come into contact with each other at the secondary stop point by relative movement of the manipulation portion body and the slider, the secondary stop point located on the proximal side in the movable range of the slider with respect to the primary stop point, and ii) by pulling the slider toward the proximal side, at least a part of the slider comes into contact with at least a part of the manipulation portion body at the secondary stop point to stop movement of the slider in the proximal direction.

3. The endoscopic treatment instrument according to claim 2, wherein, the endoscopic treatment instrument for test is configured such that when the slider is located at the secondary stop point, a distal end of the conductive tip is located on the proximal side with respect to the distal end of the tubular member.

4. The endoscopic treatment instrument according to claim 1, wherein the conductive tip and the slider are configured such that when the slider is on the proximal side with respect to the primary stop point, the distal end of the conductive tip is located on the proximal side with respect to the first position.

5. The endoscopic treatment instrument according to claim 1, wherein
the manipulation portion body has a manipulation portion body side projection on a surface facing the slider,
the slider has a slider side projection on a surface facing the manipulation portion body, and
the manipulation portion body and the slider are configured such that the manipulation portion body side projection and the slider side projection contact each other at the primary stop point or the secondary stop point.

6. An endoscopic treatment instrument comprising:
a tubular member having a distal end and a proximal end and having an inner cavity extending in a long axis direction;
a linear member having a distal end and a proximal end, extending in the long axis direction, and disposed in the inner cavity of the tubular member;
a conductive tip provided on a distal side of the linear member; and
a manipulation portion provided on a proximal side of the linear member, wherein
the manipulation portion has a manipulation portion body to which a proximal end portion of the tubular member is fixed, and a slider to which a proximal end portion of the linear member is fixed and which is disposed in the manipulation portion body and slidable relative to the manipulation portion body in the long axis direction,
the conductive tip is configured to protrude from the tubular member by moving the slider from the proximal side to the distal side,
the conductive tip has an enlarged portion having a maximum outer diameter larger than a minimum inner diameter of the tubular member, on the proximal side of the conductive tip,
the tubular member has a contact portion which comes into contact with a distal end of the enlarged portion,
the manipulation portion body has a manipulation portion body side projection,
the slider has a slider side projection, and
the tubular member, the manipulation portion body, the slider, and the conductive tip are configured such that:
when the slider side projection is located on the proximal side with respect to the manipulation portion body side projection and the manipulation portion body side projection and the slider side projection are spaced apart from each other by a distance equal to or larger than a predetermined distance, the enlarged portion and the contact portion are not in contact with each other;
when the slider side projection is located on the proximal side with respect to the manipulation portion body side projection and the manipulation portion body side projection and the slider side projection are spaced apart from each other by a distance less than the predetermined distance, the enlarged portion and the contact portion are in contact with each other; and
when the slider side projection is located on the proximal side with respect to the manipulation portion body side projection and the manipulation portion body side projection and the slider side projection are in contact with each other, the enlarged portion and the contact portion are in contact with each other.

7. The endoscopic treatment instrument according to claim 6, wherein, when the slider side projection is located on the distal side with respect to the manipulation portion body side projection, the enlarged portion and the contact portion are in contact with each other.

8. The endoscopic treatment instrument according to claim 6, wherein
in a state where a distal side surface of the manipulation portion body side projection and a proximal side surface of the slider side projection are in contact with each other, a distal end portion of the conductive tip is located at a first position located on the distal side with respect to the distal end of the tubular member, and
in a state where a proximal side surface of the manipulation portion body side projection and a distal side surface of the slider side projection are in contact with each other, the distal end portion of the conductive tip is located at the first position.

9. The endoscopic treatment instrument according to claim 6, wherein, the tubular member, the slider, and the conductive tip are configured such that when the slider is moved to a most proximal position in a movable range thereof, a distal end of the conductive tip is located on the proximal side with respect to the distal end of the tubular member.

10. The endoscopic treatment instrument according to claim 6, wherein the manipulation portion body and the slider are configured such that a force required for moving the slider side projection from the distal side of the manipulation portion body side projection to the proximal side is larger than a force required for moving the slider side projection from the proximal side of the manipulation portion body side projection to the distal side.

11. The endoscopic treatment instrument according to claim 6, wherein
the slider side projection has a tapered portion on a distal side surface thereof and has no tapered portion on a proximal side surface thereof, and
the manipulation portion body side projection has a tapered portion on a proximal side surface thereof and has no tapered portion on a distal side surface thereof.

12. The endoscopic treatment instrument according to claim 6, wherein at least either one of the linear member and the conductive tip has a length absorption portion which shortens a length in the long axis direction of at least either one of the linear member and the conductive tip when a force is applied from the proximal side toward the distal side.

13. The endoscopic treatment instrument according to claim 6, wherein the manipulation portion body has no projection on the proximal side with respect to the manipulation portion body side projection.

* * * * *